(12) United States Patent
Kim

(10) Patent No.: US 10,561,703 B2
(45) Date of Patent: *Feb. 18, 2020

(54) METHOD OF MODULATING SEX HORMONE LEVELS USING A SEX HORMONE SECRETION MODULATOR

(71) Applicants: GEMVAX & KAEL CO., LTD., Daejeon (KR); Sang Jae Kim, Gangnam-gu, Seoul (KR)

(72) Inventor: Sang Jae Kim, Seoul (KR)

(73) Assignee: GemVaX & KAEL Co., Ltd., Deajeon (KR)

(*) Notice: Subject to any disclaimer, the term of this patent is extended or adjusted under 35 U.S.C. 154(b) by 0 days.

This patent is subject to a terminal disclaimer.

(21) Appl. No.: 14/899,746

(22) PCT Filed: Jun. 23, 2014

(86) PCT No.: PCT/KR2014/005508
§ 371 (c)(1),
(2) Date: Dec. 18, 2015

(87) PCT Pub. No.: WO2014/204281
PCT Pub. Date: Dec. 24, 2014

(65) Prior Publication Data
US 2016/0137695 A1 May 19, 2016

(30) Foreign Application Priority Data

Jun. 21, 2013 (EP) .................................. 13173219

(51) Int. Cl.
| | |
|---|---|
| *A61K 38/10* | (2006.01) |
| *A61K 39/39* | (2006.01) |
| *A61K 38/45* | (2006.01) |
| *C12N 9/12* | (2006.01) |
| *C07K 14/575* | (2006.01) |
| *C07K 7/08* | (2006.01) |

(52) U.S. Cl.
CPC .............. *A61K 38/10* (2013.01); *A61K 39/39* (2013.01); *A61K 38/45* (2013.01); *C07K 7/08* (2013.01); *C07K 14/575* (2013.01); *C12N 9/1276* (2013.01); *C12Y 207/07049* (2013.01)

(58) Field of Classification Search
None
See application file for complete search history.

(56) References Cited

U.S. PATENT DOCUMENTS

| | | | |
|---|---|---|---|
| 6,967,211 B2 | 11/2005 | Inoue | |
| 7,030,211 B1 * | 4/2006 | Gaudernack | ............ A61K 38/45 424/184.1 |
| 7,786,084 B2 | 8/2010 | Benner et al. | |
| 7,794,723 B2 | 9/2010 | Gaudernack et al. | |
| 8,828,403 B2 | 9/2014 | Filaci et al. | |
| 8,933,197 B2 | 1/2015 | Bogin et al. | |
| 9,023,987 B2 | 5/2015 | Chung et al. | |
| 9,540,419 B2 | 1/2017 | Kim et al. | |
| 9,572,858 B2 * | 2/2017 | Kim | ..................... A61K 38/10 |
| 9,937,240 B2 | 4/2018 | Kim et al. | |
| 2002/0042401 A1 | 4/2002 | Ferguson et al. | |
| 2003/0027769 A1 | 2/2003 | Scialdone et al. | |
| 2003/0143228 A1 | 7/2003 | Chen et al. | |
| 2006/0106196 A1 | 5/2006 | Gaudernack et al. | |
| 2007/0190561 A1 | 8/2007 | Morin et al. | |
| 2008/0025986 A1 | 1/2008 | Ozes et al. | |
| 2009/0136917 A1 | 5/2009 | Szalay et al. | |
| 2009/0186802 A1 | 7/2009 | Alluis et al. | |
| 2009/0215852 A1 | 8/2009 | Bascomb et al. | |
| 2011/0135692 A1 | 6/2011 | Filaci et al. | |
| 2011/0150873 A1 | 6/2011 | Grainger | |
| 2011/0183925 A1 | 7/2011 | Sato et al. | |
| 2012/0053134 A1 | 3/2012 | Jung et al. | |
| 2012/0065124 A1 | 3/2012 | Morishita et al. | |
| 2012/0208755 A1 | 8/2012 | Leung | |
| 2012/0277290 A1 | 11/2012 | Collard et al. | |
| 2013/0129760 A1 | 5/2013 | Gaudernack et al. | |
| 2013/0230591 A1 | 9/2013 | Fellous et al. | |
| 2015/0099692 A1 | 4/2015 | Kim et al. | |

(Continued)

FOREIGN PATENT DOCUMENTS

| | | | |
|---|---|---|---|
| EP | 1020190 A3 | 10/2000 | |
| EP | 1093381 B2 | 7/2009 | |

(Continued)

OTHER PUBLICATIONS

Hormones, in MeSH Database, National Center for Biotechnology Information, Bethesda, Maryland, USA [online], [retrieved on May 8, 2017]. Retrieved from the Internet: <URL: http://www.ncbi.nlm.nih.gov/mesh/68006728>.*

Beer, T.M., et al., "Phase II Study of Weekly Docetaxel in Symptomatic Androgen-independent Prostate Cancer," Annals of Oncology 12(9):1273-1279, Oxford University Press, England (2001).

Bohonowych, J.E., et al., "Comparative Analysis of Novel and Conventional HSP90 Inhibitors on HIF Activity and Angiogenic Potential in Clear Cell Renal Cell Carcinoma: Implications for Clinical Evaluation," BMC Cancer 11:520, BioMed Central, England (2011).

(Continued)

Primary Examiner — Christine J Saoud
(74) Attorney, Agent, or Firm — Sterne, Kessler, Goldstein & Fox, P.L.L.C.

(57) ABSTRACT

Provided are a hormone secretion modulator including a peptide derived from telomerase, more particularly, a peptide including an amino acid sequence of SEQ ID NO: 1, an amino acid sequence having a sequence identity of at least 80% with SEQ ID NO: 1, or a fragment thereof, a pharmaceutical composition including the hormone secretion modulator, and a use of the pharmaceutical composition for treatment, alleviation, or prevention of diseases caused by excessive or deficient levels hormones.

20 Claims, 5 Drawing Sheets
Specification includes a Sequence Listing.

(56) References Cited

U.S. PATENT DOCUMENTS

| | | |
|---|---|---|
| 2015/0099693 A1 | 4/2015 | Kim et al. |
| 2015/0175978 A1 | 6/2015 | Kim |
| 2015/0307859 A1 | 10/2015 | Kim |
| 2015/0343095 A1 | 12/2015 | Kim |
| 2015/0353903 A1 | 12/2015 | Kim |
| 2016/0002613 A1 | 1/2016 | Kim |
| 2016/0008438 A1 | 1/2016 | Kim |
| 2016/0082089 A1 | 3/2016 | Kim |
| 2016/0120966 A1 | 5/2016 | Kim |
| 2016/0151512 A1 | 6/2016 | Kim |
| 2016/0250279 A1 | 9/2016 | Kim |
| 2016/0296604 A1 | 10/2016 | Kim |
| 2016/0375091 A1 | 12/2016 | Kim |
| 2017/0028035 A1 | 2/2017 | Kim |
| 2017/0058001 A1 | 3/2017 | Kim |
| 2017/0081376 A1 | 3/2017 | Kim et al. |
| 2017/0128557 A1 | 5/2017 | Kim et al. |
| 2017/0143806 A1 | 5/2017 | Kim et al. |
| 2017/0275603 A1 | 9/2017 | Kim et al. |
| 2017/0360870 A1 | 12/2017 | Kim |

FOREIGN PATENT DOCUMENTS

| | | |
|---|---|---|
| EP | 1817337 B1 | 1/2011 |
| EP | 3372613 A1 | 9/2018 |
| JP | 2002522373 A | 7/2002 |
| JP | 2010252810 A | 11/2010 |
| JP | 2012526524 A | 11/2012 |
| JP | 5577472 B2 | 8/2014 |
| KR | 19930001915 A | 2/1993 |
| KR | 20010012613 A | 2/2001 |
| KR | 20010020601 A | 3/2001 |
| KR | 20040015087 A | 2/2004 |
| KR | 20040045400 A | 6/2004 |
| KR | 20040107492 A | 12/2004 |
| KR | 20050020987 A | 3/2005 |
| KR | 20050040517 A | 5/2005 |
| KR | 20060065588 A | 6/2006 |
| KR | 20060109903 A | 10/2006 |
| KR | 20070083218 A | 8/2007 |
| KR | 20080084818 A | 9/2008 |
| KR | 20090033878 A | 4/2009 |
| KR | 20090103957 A | 10/2009 |
| KR | 20100058541 A | 6/2010 |
| KR | 20100085527 A | 7/2010 |
| KR | 20110057049 A | 5/2011 |
| KR | 20110060940 A | 6/2011 |
| KR | 20110062943 A | 6/2011 |
| KR | 20110130943 A | 12/2011 |
| KR | 20120018188 A | 2/2012 |
| KR | 20120026408 A | 3/2012 |
| KR | 20120035150 A | 4/2012 |
| KR | 20120087885 A | 8/2012 |
| KR | 20120121196 A | 11/2012 |
| KR | 20120130996 A | 12/2012 |
| KR | 20120133661 A | 12/2012 |
| KR | 20130004949 A | 1/2013 |
| KR | 20130041896 A | 4/2013 |
| KR | 20140037698 A | 3/2014 |
| WO | WO-0002581 A1 | 1/2000 |
| WO | WO-2010003520 A2 | 1/2010 |
| WO | WO-2010012850 A1 | 2/2010 |
| WO | WO-2010128807 A2 | 11/2010 |
| WO | WO-2011101173 A1 | 8/2011 |
| WO | WO-2011150494 A1 | 12/2011 |
| WO | WO-2013100500 A1 | 7/2013 |
| WO | WO-2013118899 A1 | 8/2013 |
| WO | WO-2013135266 A1 | 9/2013 |
| WO | WO-2013167574 A1 | 11/2013 |
| WO | WO-2013169060 A1 | 11/2013 |
| WO | WO-2013169067 A1 | 11/2013 |
| WO | WO-2013169077 A1 | 11/2013 |
| WO | WO-2014010971 A1 | 1/2014 |
| WO | WO-2014012683 A1 | 1/2014 |
| WO | WO-2014046478 A1 | 3/2014 |
| WO | WO-2014046481 A1 | 3/2014 |
| WO | WO-2014046490 A1 | 3/2014 |
| WO | WO-2014046983 A1 | 3/2014 |
| WO | WO-2014171792 A1 | 10/2014 |
| WO | WO-2014196841 A1 | 12/2014 |
| WO | WO-2015060673 A1 | 4/2015 |
| WO | WO-2015076621 A1 | 5/2015 |
| WO | WO-2015093854 A1 | 6/2015 |
| WO | WO-2015156649 A1 | 10/2015 |
| WO | WO-2015167067 A1 | 11/2015 |
| WO | WO-2016105086 A1 | 6/2016 |
| WO | WO-2016137162 A1 | 9/2016 |
| WO | WO-2017078440 A1 | 5/2017 |

OTHER PUBLICATIONS

Bruns, A.F., et al., "A Heat-shock Protein Axis Regulates VEGFR2 Proteolysis, Blood Vessel Development and Repair," PloS One 7(11):e48539, Public Library of Science, United States (2012).

Calderwood, S.K., et al., "Heat Shock Proteins in Cancer: Chaperones of Tumorigenesis," Trends in Biochemical Sciences 31(3):164-172, Elsevier Trends Journals, England (2006).

Dempsey, N.C., et al., "Differential Heat Shock Protein Localization in Chronic Lymphocytic Leukemia," Journal of Leukocyte Biology 87(3):467-476, Society for Leukocyte Biology, United States (2010).

Du, R., et al., "HIF1alpha Induces the Recruitment of Bone Marrow-derived Vascular Modulatory Cells to Regulate Tumor Angiogenesis and Invasion," Cancer Cell 13(3):206-220, Cell Press, United States (2008).

Eustace, B.K. and Jay, D.G., "Extracellular Roles for the Molecular Chaperone, Hsp90," Cell Cycle 3(9):1098-1100, Taylor & Francis, United States (2004).

Eustace, B.K. and Jay, D.G., "Functional Proteomic Screens Reveal an Essential Extracellular Role for Hsp90 Alpha in Cancer Cell Invasiveness," Nature Cell Biology 6(6):507-514, Macmillan Magazines Ltd., England (2004).

Evans, C.G., et al., "Heat Shock Protein 70 (Hsp70) as an Emerging Drug Target," Journal of Medicinal Chemistry 53(12):4585-4602, American Chemical Society, United States (2010).

Ferrarini, M., et al., "Unusual Expression and Localization of Heat-shock Proteins in Human Tumor Cells," International Journal of Cancer51(4):613-619, Wiley-Liss, United States (1992).

Garcia-Carbonero, R., et al., "Inhibition of HSP90 Molecular Chaperones: Moving Into the Clinic," The Lancet Oncology 14(9):e358-e369, Lancet Publishing Group, England (2013).

Henry, J.Y., et al., "Lenalidomide Enhances the Anti-prostate Cancer Activity of Docetaxel in vitro and in vivo," The Prostate 72(8):856-867, Wiley-Liss, United States (2012).

International Preliminary Report on Patentability for International Application No. PCT/KR2014/011280, The International Bureau of WIPO, Geneva, Switzerland, dated May 24, 2016, 15 pages.

International Search Report for International Application No. PCT/KR2014/011280, Korean Intellectual Property Office, Republic of Korea, dated Feb. 11, 2015, 12 pages.

International Search Report for International Application No. PCT/KR2014/012502, Korean Intellectual Property Office, Republic of Korea, dated Mar. 11, 2015, 10 pages.

International Preliminary Report on Patentability for International Application No. PCT/KR2014/012502, The International Bureau of WIPO, Geneva, Switzerland, dated Jun. 21, 2016, 22 pages.

Jaattela, M., "Over-expression of Hsp70 Confers Tumorigenicity to Mouse Fibrosarcoma Cells," International Journal of Cancer 60(5):689-693, Wiley-Liss, United States (1995).

Jemal, A., et al., "Cancer Statistics, 2008," CA: A Cancer Journal for Clinicians 58(2):71-96, Wiley, United States (2008).

Kim, B.K., et al., "Tumor-suppressive Effect of a Telomerase-derived Peptide by Inhibiting Hypoxia-induced HIF-1α-VEGF Signaling Axis," Biomaterials 35(9):2924-2933, Elsevier Science, Netherlands (2014).

Kocsis, J., et al., "Serum Level of Soluble 70-kD Heat Shock Protein is Associated With High Mortality in Patients With Colorectal Cancer Without Distant Metastasis," Cell Stress & Chaperones 15(2):143-151, Springer, Netherlands (2010).

(56) References Cited

OTHER PUBLICATIONS

Liu, Q.J., et al., "Rapamycin Enhances the Susceptibility of Both Androgen-dependent and -independent Prostate Carcinoma Cells to Docetaxel," Chinese Medical Journal 123(3):356-360, Chinese Medical Association, China (2010).
Morano, K.A., "New Tricks for an Old Dog: the Evolving World of Hsp70," Annals of the New York Academy of Sciences 1113:1-14, Blackwell, United States (2007).
Murphy, M.E., "The Hsp70 Family and Cancer," Carcinogenesis 34(6):1181-1188, Irl Press, England (2013).
Nagaraju, G.P., et al., "Antiangiogenic Effects of Ganetespib in Colorectal Cancer Mediated Through Inhibition of HIF-1α and STAT-3," Angiogenesis 16(4):903-917, Springer, Germany (2013).
Pfosser, A., et al., "Liposomal HSP90 Cdna Induces Neovascularization via Nitric Oxide in Chronic Ischemia," Cardiovascular Research 65(3):728-736, Oxford Journals, England (2005).
Powers, M.V., et al., "Targeting HSP70: the Second Potentially Druggable Heat Shock Protein and Molecular Chaperone?," Cell Cycle 9(8):1542-1550, Taylor & Francis, United States (2010).
Sayers, S., et al., "Vaxjo: A Web-based Vaccine Adjuvant Database and its Application for Analysis of Vaccine Adjuvants and their Uses in Vaccine Development," Journal of Biomedicine and Biotechnology 2012:1-13, Article ID 831486, Hindawi Publishing Corporation, United States (2012).
Seo, J.S., et al., "T Cell Lymphoma in Transgenic Mice Expressing the Human Hsp70 Gene," Biochemical and Biophysical Research Communications 218(2):582-587, Elsevier, United States (1996).
Sun, J., et al., "Induction of Angiogenesis by Heat Shock Protein 90 Mediated by Protein Kinase Akt and Endothelial Nitric Oxide Synthase," Arteriosclerosis, Thrombosis, and Vascular biology 24(12):2238-2244, Lippincott Williams & Wilkins, United States (2004).
Uehara, Y., "Natural Product Origins of Hsp90 Inhibitors," Current Cancer Drug Targets 3(5):325-330, Bentham Science Publishers, Netherlands (2003).
Vanbuskirk, A., et al., "A Peptide Binding Protein Having a Role in Antigen Presentation is a Member of the HSP70 Heat Shock Family," The Journal of Experimental Medicine 170(6):1799-1809, Rockefeller University Press, United States (1989).
Volloch, V.Z. and Sherman, M.Y., "Oncogenic Potential of Hsp72," Oncogene 18(24):3648-3651, Nature Publishing Group, England (1999).
Written Opinion for International Application No. PCT/KR2014/011280, Korean Intellectual Property Office, Republic of Korea, dated Feb. 11, 2015, 14 pages.
Written Opinion for International Application No. PCT/KR2014/012502, Korean Intellectual Property Office, Republic of Korea, dated Mar. 11, 2015, 20 pages.
Yeh, C.H., et al., "Clinical Correlation of Circulating Heat Shock Protein 70 in Acute Leukemia," Leukemia Research 34(5):605-609, Pergamon Press, England (2010).
Zhou, J., et al., "PI3K/Akt is Required for Heat Shock Proteins to Protect Hypoxia-inducible Factor 1alpha From pVHL-independent Degradation," The Journal of Biological Chemistry 279(14):13596-13513, American Society for Biochemistry and Molecular Biology, United States (2004).
Dementia from Merck Manual, accessed on Jul. 29, 2009, pp. 1-17.
Mattson, M.P., "Pathways Towards and Away From Alzheimer's Disease," Nature 430(7000):631-639, Nature Publishing Group, England (2004).
McConnell, J.D., et al., "The Effect of Finasteride on the Risk of Acute Urinary Retention and the Need for Surgical Treatment Among Men with Benign Prostatic Hyperplasia. Finasteride Long-term Efficacy and Safety Study Group," The New England Journal of Medicine 338(9):557-563, Massachusetts Medical Society, United States (1998).
Perez, R.G., et al., "The Beta-amyloid Precursor Protein of Alzheimer's Disease Enhances Neuron Viability and Modulates Neuronal Polarity," The Journal of Neuroscience 17(24):9407-9414, Society for Neuroscience, United States (1997).

Rheumatoid Arthritis from Merck Manual, accessed on Apr. 21, 2016, pp. 1-18.
Schenk, D., et al., "Immunization with Amyloid-beta Attenuates Alzheimer-disease-like Pathology in the PDAPP Mouse," Nature 400(6740):173-177, Nature Publishing Group, England (1999).
Van Coppenolle, F., et al., "Effects of Hyperprolactinemia on Rat Prostate Growth: Evidence of Androgeno-dependence," American Journal of Physiology. Endocrinology and Metabolism 280(1):E120-E129, American Physiological Society, United States (2001).
Altschul, S.F., et al., "Basic Local Alignment Search Tool," Journal of Molecular Biology 215(3):403-410, Elsevier, England (1990).
Bernhardt, S.L., et al., "Telomerase Peptide Vaccination of Patients with Non-Resectable Pancreatic Cancer: A Dose Escalating Phase I/II Study," British Journal of Cancer 95(11):1474-1482, Nature Publishing Group on behalf of Cancer Research, England (2006).
Bonaldi, T., et al., "Monocytic Cells Hyperacetylate Chromatin Protein HMGB1 to Redirect it Towards Secretion," The EMBO Journal 22(20):5551-5560, Wiley Blackwell, England (2003).
Brandenburg, K., et al., "Peptide-based Treatment of Sepsis," Applied Microbiology and Biotechnology 90(3):799-808, Springer International, Germany (2011).
Brunsvig, P.F., et al., "Telomerase Peptide Vaccination in NSCLC: A Phase II Trial in Stage III Patients Vaccinated after Chemoradiotherapy and an 8-year Update on a Phase I/II Trial," Clinical Cancer Research 17(21):6847-6857, The Association, United States (2011).
Cho, Y.J., "GemVax & Kael (082270)," Hana Daetoo Securities, Company Report, Sep. 10, 2012, 8 pages.
Choi, S.G., "Recent Advances in Cancer Cachexia," Journal of Korean Oncology Nursing 11(1):20-25 (2011).
Co-pending U.S. Appl. No. 14/413,732, inventor Sang Jae Kim, filed Jul. 11, 2013 (Not Published).
Co-pending U.S. Appl. No. 14/896,358, inventor Sang Jae Kim, filed Dec. 4, 2015 (Not Published).
Co-pending U.S. Appl. No. 14/899,746, inventor Sang Jae Kim, filed Apr. 12, 2015 (Not Published).
Dahlgren, K.N., et al., "Oligomeric and *Fibrillar* Species of Amyloid-beta Peptides Differentially Affect Neuronal Viability," Journal of Biological Chemistry 277(35):32046-32053, American Society for Biochemistry and Molecular Biology, United States (2002).
Dinarello, C.A., "Interleukin-1 in the Pathogenesis and Treatment of Inflammatory Diseases," Blood 117(14):3720-3732, American Society of Hematology, United States (2011).
Engineer, D.R. and Garcia, J.M., "Leptin in Anorexia and Cachexia Syndrome," International Journal of Peptides 2012:Article ID 287457, Hindawi Publishing Corporation, United States (2012).
Fire, A., et al., "Potent and Specific Genetic Interference by Double-stranded RNA in Caenorhabditis Elegans," Nature 391(6669):806-811, Nature Publishing Group, England (1998).
Fittipaldi, A., et al., "Cell Membrane Lipid Rafts Mediate Caveolar Endocytosis of HIV-1 Tat Fusion Proteins," Journal of Biological Chemistry 278(36): 34141-34149, American Society for Biochemistry and Molecular Biology, United (2003).
Fonseca, S.B., et al., "Recent Advances in the Use of Cell-Penetrating Peptides for Medical and Biological Applications," Advanced Drug Delivery Reviews 61(11):953-964, Elsevier Science Publishers, Netherlands (2009).
Fujii, H., et al., "Telomerase Insufficiency in Rheumatoid Arthritis," Proceedings of the National Academy of Sciences USA 106(11):4360-4365, National Academy of Sciences, United States (2009).
GemVax Receives Report on Anti-Inflammatory Mechanism, The Asia Economy Daily, Article written on May 7, 2013.
Ghaneh, P., et al., "Biology and Management of Pancreatic Cancer," Gut 56(8):1134-1152, British Medical Association, England (2007).
Granger, D.N. and Korthuis, R.J., "Physiologic Mechanisms of Postischemic Tissue Injury," Annual Review of Physiology 57:311-332, Annual Reviews, United States (1995).
Gunturu, K.S., et al., "Immunotherapy Updates in Pancreatic Cancer: Are we there yet?," Therapeutic Advances in Medical Oncology 5(1):81-89, Sage, England (2013).
Heitz, F., et al., "Twenty Years of Cell-Penetrating Peptides: From Molecular Mechanisms to Therapeutics," British Journal of Pharmacology 157(2):195-206, Wiley, England (2009).

(56) References Cited

OTHER PUBLICATIONS

Hse, "Rheumatoid arthritis," http://www.hse.ie/portal/eng, accessed at http://www.hse.ie/portal/eng/health/az/R/Rheumatoid-arthritis/, 14 pages (2013).
Inderberg-Suso, E.M., et al., "Widespread CD4+ T-cell Reactivity to Novel hTERT Epitopes following Vaccination of Cancer Patients with a Single hTERT Peptide GV1001," Oncoimmunology 1(5):670-686, Taylor & Francis, United States (2012).
International Preliminary Report on Patentability for International Application No. PCT/EP2013/059460, International Bureau of WIPO, Switzerland, dated Nov. 11, 2014, 5 pages.
International Preliminary Report on Patentability for International Application No. PCT/KR2013/004145, The International Bureau of WIPO, Switzerland, dated Nov. 11, 2014, 14 pages.
International Preliminary Report on Patentability for International Application No. PCT/KR2013/004176, The International Bureau of WIPO, Switzerland, dated Nov. 11, 2014, 14pages.
International Preliminary Report on Patentability for International Application No. PCT/KR2013/006218, The International Bureau of WIPO, Switzerland, dated Jan. 13, 2015, 27 pages.
International Preliminary Report on Patentability for International Application No. PCT/KR2013/008438, The International Bureau of WIPO, Switzerland, dated Mar. 24, 2015, 10 pages.
International Preliminary Report on Patentability for International Application No. PCT/KR2013/008445, The International Bureau of WIPO, Switzerland, dated Mar. 24, 2015, 13 pages.
International Preliminary Report on Patentability for International Application No. PCT/KR2014/003425, The International Bureau of WIPO, Switzerland, dated Oct. 20, 2015, 14 pages.
International Preliminary Report on Patentability for International Application No. PCT/KR2014/005031, The International Bureau of WIPO, Switzerland, dated Dec. 8, 2015, 8 pages.
International Preliminary Report on Patentability for International Application No. PCT/KR2014/005508, The International Bureau of WIPO, Switzerland, dated Jan. 5, 2016, 14 pages.
International Preliminary Report on Patentability for International Patent Application No. PCT/KR2013/004156, The International Bureau of WIPO, Geneva, Switzerland, dated Nov. 11, 2014, 15 pages.
International Search Report for International Application No. PCT/KR2014/003425, Korean Intellectual Property Office, Republic of Korea, dated Jul. 21, 2014, 8 pages.
International Search Report for International Application No. PCT/EP2013/059460, European Patent Office, Netherlands, dated Jul. 3, 2013, 5 pages.
International Search Report for International Application No. PCT/KR2013/004145, Korean Intellectual Property Office, Republic of Korea, dated Aug. 14, 2013, 10 pages.
International Search Report for International Application No. PCT/KR2013/004176, Korean Intellectual Property Office, Republic of Korea, dated Aug. 6, 2013, 10 pages.
International Search Report for International Application No. PCT/KR2013/006218, Korean Intellectual Property Office, Republic of Korea, dated Sep. 26, 2013, 8 pages.
International Search Report for International Application No. PCT/KR2013/008438, Korean Intellectual Property Office, Republic of Korea, dated Dec. 23, 2013, 8 pages.
International Search Report for International Application No. PCT/KR2013/008445, Korean Intellectual Property Office, Republic of Korea, dated Dec. 23, 2013, 10 pages.
International Search Report for International Application No. PCT/KR2014/005031, Korean Intellectual Property Office, Republic of Korea, dated Sep. 22, 2014, 6 pages.
International Search Report for International Application No. PCT/KR2014/005508, Korean Intellectual Property Office, Republic of Korea, dated Oct. 14, 2014, 8 pages.
International Search Report for International Application No. PCT/KR2014/010035, Korean Intellectual Property Office, Republic of Korea, dated Feb. 2, 2015, 8 pages.
International Search Report for International Patent Application No. PCT/KR2013/004156, Korean Intellectual Property Office, Republic of Korea, dated Aug. 14, 2013, 10 pages.
International Search Report for International Application No. PCT/KR2013/008459, Korean Intellectual Property Office, Republic of Korea, dated Dec. 23, 2013, 8 pages.
Kern, K.A. and Norton, J.A., "Cancer Cachexia," Journal of Parenteral and Enteral Nutrition 12(3):286-298, Sage Publications, United States (1988).
Kim, H.O. and Lee, S.I., "Experimental Animal Models for Rheumatoid Arthritis: Methods and Applications," Journal of Rheumatic Diseases 19(4):189-195, The Korean College of Rheumatology, Republic of Korea(2012).
Kokhaei, P., et al., "Telomerase (hTERT 611-626) Serves as a Tumor Antigen in B-cell Chronic Lymphocytic Leukemia and Generates Spontaneously Antileukemic, Cytotoxic T Cells," Experimental Hematology 35(2):297-304, Elsevier Science Inc., Netherlands (2007).
Kyte, J.A., "Cancer Vaccination with Telomerase Peptide GV1001," Expert Opinion on Investigational Drugs 18(5):687-694, Taylor & Francis, England (2009).
Lahdevirta, J., et al., "Elevated Levels of Circulating Cachectin/tumor Necrosis Factor in Patients with Acquired Immunodeficiency Syndrome," American Journal of Medicine 85(3):289-291, Excerpta Medica, United States (1988).
Laviano, A., et al., "Therapy Insight: Cancer Anorexia-cachexia Syndrome—When All You Can Eat is Yourself," Nature Clinical Practice. Oncology 2(3):158-165, Nature Publishing Group, England (2005).
Lee, S.A., et al., "Heat Shock Protein-Mediated Cell Penetration and Cytosolic Delivery of Macromolecules by a Telomerase-Derived Peptide Vaccine," Biomaterials 34(30):7495-7505, Elsevier Science, Netherlands (2013).
Luft, R., et al., "A Case of Severe Hypermetabolism of Nonthyroid Origin with a Defect in the Maintenance of Mitochondrial Respiratory Control: A Correlated Clinical, Biochemical, and Morphological Study," Journal of Clinical Investigation 41:1776-1804, American Society for Clinical Investigation, United States (1962).
Martinez, P. and Blasco, M.A., "Telomeric and Extra-telomeric Roles for Telomerase and the Telomere-binding Proteins," Nature Reviews Cancer 11(3):161-176, Nature Publishing Group, England (2011).
Modica-Napolitano, J.S. and Singh, K.K., "Mitochondria as Targets for Detection and Treatment of Cancer," Expert Reviews in Molecular Medicine 4(9):1-19, Cambridge University Press, England (2002).
Myers, L.K., et al., "Collagen-Induced Arthritis, an Animal Model of Autoimmunity," Life Sciences 61(19):1861-1878, Elsevier, Netherlands (1997).
National Horizon Scanning Centre News on Emerging Technologies in Healthcare, GV1001 for Advanced and/or Metastatic Pancreatic Cancer, Published Apr. 2008.
NCBI, Reference Sequence: XP_003776612.1 (Jul. 17, 2012).
Novina, C.D. and Sharp, P.A., "The RNAi Revolution," Nature 430(6996):161-164, Nature Publishing Group, England (2004).
Oh, H., et al., "Telomerase Reverse Transcriptase Promotes Cardiac Muscle Cell Proliferation, Hypertrophy, and Survival," Proceedings of the National Academy of Sciences 98(18): 10308-10313, National Academy of Sciences, United States (2001).
Pearson, W.R. and Lipman, D.J., "Improved Tools for Biological Sequence Comparison," Proceedings of the National Academy of Sciences USA 85(8):2444-2448, National Academy of Sciences, United States (1988).
Rana, T.M., "Illuminating the Silence: Understanding the Structure and Function of Small RNAs," Nature Reviews. Molecular Cell Biology 8(1):23-36, Nature Publishing Group, England (2007).
Roubenoff, R., et al., "Adjuvant Arthritis as a Model of Inflammatory Cachexia," Arthritis and Rheumatism 40(3):534-539, Wiley-Blackwell, United States (1997).
Schlapbach, C., et al., "Telomerase-specific GV1001 Peptide Vaccination Fails to Induce Objective Tumor Response in Patients with Cutaneous T Cell Lymphoma," Journal of Dermatological Science 62(2):75-83, Elsevier, Netherlands (2011).

(56) References Cited

OTHER PUBLICATIONS

Shay, J.W., and Wright, W.E., "Telomerase Therapeutics for Cancer: Challenges and New Directions," Nature Reviews. Drug Discovery 5(7):577-584, Nature Publishing Group, England (2006).
Smith, D.B. and Johnson, K.S., "Single-step Purification of Polypeptides Expressed in *Escherichia coli* as Fusions with Glutathione S-transferase," Gene 67(1):31-40, Elsevier, Netherlands (1988).
Smith, T.F. and Waterman, M.S., "Comparison of Biosequences," Advances in Applied Mathematics 2(4):482-489, Academic Press, Inc., United States (1981).
Southern Cross, "Rheumatoid arthritis—causes, symptoms, and treatment," https://www.southerncross.co.nz/, accessed at https://www.southerncross.co.nz/AboutTheGroup/HealthResources/MedicalLibrary/tabid/178/vw/1/itemID/124/Rheumatoid-arthritis-causes-symptoms-treatment.aspx, last reviewed on May 31, 2013, 5 pages.
Stevenson, C.L., "Advances in Peptide Pharmaceuticals," Current Pharmaceutical Biotechnology 10(1):122-137, Bentham Science Publishers, United Arab Emirates (2009).
Taylor, P.C. and Feldmann, M., "Anti-TNF Biologic Agents: Still the Therapy of Choice for Rheumatoid Arthritis," Nature Reviews. Rheumatology 5(10):578-582, Macmillan Publishers Limited, England (2009).
Thompson, J.D., et al., "Clustal W: Improving the Sensitivity of Progressive Multiple Sequence Alignment Through Sequence Weighting, Position-specific Gap Penalties and Weight Matrix Choice," Nucleic Acids Research 22(22):4673-4680, Oxford University Press, England (1994).
Tisdale, M.J., "Mechanisms of Cancer Cachexia," Physiological Reviews 89(2):381-410, American Physiological Society, United States (2009).
Tomari Y. and Zamore, P.D., "Perspective: Machines for RNAi," Genes and Development 19(5):517-529, Cold Spring Harbor Laboratory Press, United States (2005).
Vennela, B., et al., "Current and Future Strategies for Therapy of Pancreatic Cancer," International Journal of Research in Pharmacy and Medicine 2(3):728-740 (2012).
Walsmith, J. and Roubenoff, R., "Cachexia in Rheumatoid Arthritis," International Journal of Cardiology 85(1):89-99, Elsevier, Netherlands (2002).
Written Opinion for International Application No. PCT/EP2013/059460, European Patent Office, Germany, dated Jul. 3, 2013, 4 pages.
Written Opinion for International Application No. PCT/KR2013/004145, Korean Intellectual Property Office, Republic of Korea, dated Aug. 14, 2013, 13 pages.
Written Opinion for International Application No. PCT/KR2013/004176, Korean Intellectual Property Office, Republic of Korea, dated Aug. 6, 2013, 13 pages.
Written Opinion for International Application No. PCT/KR2013/006218, Korean Intellectual Property Office, Republic of Korea, dated Sep. 26, 2013, 26 pages.
Written Opinion for International Application No. PCT/KR2013/008438, Korean Intellectual Property Office, Republic of Korea, dated Dec. 23, 2013, 9 pages.
Written Opinion for International Application No. PCT/KR2013/008445, Korean Intellectual Property Office, Republic of Korea, dated Dec. 23, 2013, 12 pages.
Written Opinion for International Application No. PCT/KR2014/005031, Korean Intellectual Property Office, Republic of Korea, dated Sep. 22, 2014, 7 pages.
Written Opinion for International Application No. PCT/KR2014/005508, Korean Intellectual Property Office, Republic of Korea, dated Oct. 14, 2014, 13 pages.
Written Opinion for International Application No. PCT/KR2013/008459, Korean Intellectual Property Office, Republic of Korea, dated Dec. 23, 2013, 9 pages.
Written Opinion for International Patent Application No. PCT/KR2013/004156, Korean Intellectual Property Office, Republic of Korea, dated Aug. 14, 2013, 13 pages.
Written Opinion for International Application No. PCT/KR2014/003425, Korean Intellectual Property Office, Republic of Korea, dated Jul. 21, 2014, 13 pages.
Yankner, B.A., et al., "Neurotrophic and Neurotoxic Effects of Amyloid Beta Protein: Reversal by Tachykinin Neuropeptides," Science 250(4978):279-282, American Association for the Advancement of Science, United States (1990).
National Institute of Diabetes and Digestive and Kidney Diseases, "Prostate Enlargement: Benign Prostatic Hyperplasia," Updated Sep. 2014, 14 pages.
Sasada, A., et al., "A Case of Elderly Patient With Lung Cancer Efficiently Treated With Dendritic Cell Immunotherapy, "The 20th International Congress of Personalized Medicine, Conference Program and Abstracts, Personalized Medicine Universe (Japanese edition) 4(Supplement 1): 2 pages, May 24, 2015.
Shaw, V.E., et al., "Current Status of GV1001 and Other Telomerase Vaccination Strategies in the Treatment of Cancer," Expert Review of Vaccines 9(9):1007-1016, Taylor & Francis, England (2010).
Co-pending U.S. Appl. No. 15/346,870, inventors Kim, Sang Jae, filed Nov. 9, 2016 (Not Yet Published).
Heldin, C.H., et al., "TGF-Beta Signalling from Cell Membrane to Nucleus through SMAD Proteins," Nature 390(6659):465-471, Nature Publishing Group, England (1997).
International Preliminary Report on Patentability for Application No. PCT/KR2014/004752, The International Bureau of WIPO, Switzerland, dated Nov. 1, 2016, 23 pages.
International Preliminary Report on Patentability for Application No. PCT/KR2015/003642, The International Bureau of WIPO, Switzerland, dated Oct. 12, 2016, 18 pages.
International Preliminary Report on Patentability for International Application No. PCT/KR2014/010035, Korean Intellectual Property Office, Republic of Korea, dated Apr. 26, 2016, 13 pages.
International Search Report for International Application No. PCT/KR2014/004752, Korean Intellectual Property Office, Republic of Korea, dated Jan. 16, 2015, 10 pages.
International Search Report for International Application No. PCT/KR2015/003642, Korean Intellectual Property Office, Republic of Korea, dated Jul. 3, 2015, 8 pages.
Massague, J., "Tgf-Beta Signal Transduction," Annual Review of Biochemistry 67:753-791, Annual Reviews, United States (1998).
Song, J., et al., "Characterization and Fate of Telomerase-Expressing Epithelia during Kidney Repair," Journal of the American Society of Nephrology 22(12):2256-2265, American Society of Nephrology, United States (2011).
Wang, W., et al., "Alleviating the Ischemia-Reperfusion Injury of Donor Liver by Transfection of Exogenous hTERT Genes," Transplantation Proceedings 41(5):1499-1503, Elsevier Science, United States (2009).
Written Opinion for International Application No. PCT/KR2014/004752, Korean Intellectual Property Office, Republic of Korea, dated Jan. 16, 2015, 21 pages.
Written Opinion for International Application No. PCT/KR2014/010035, Korean Intellectual Property Office, Republic of Korea, dated Feb. 2, 2015, 11 pages.
Written Opinion for International Application No. PCT/KR2015/003642, Korean Intellectual Property Office, Republic of Korea, dated Jul. 3, 2015, 16 pages.
Yi, A., et al., "Radiation-Induced Complications after Breast Cancer Radiation Therapy: a Pictorial Review of Multimodality Imaging Findings," Korean Journal of Radiology 10(5):496-507, Korean Society of Radiology, Korea (2009).
Zhang, H., et al., "Inhibiting TGFβ1 has a Protective Effect on Mouse Bone Marrow Suppression Following Ionizing Radiation Exposure in Vitro," Journal of Radiation Research 54(4):630-636, Oxford University Press, England (2013).
Eisenegger, C., et al., "The Role of Testosterone in Social Interaction," Trends in Cognitive Sciences 15(6):263-271, Elsevier Science, England (2011).
"Seoul National University Bundang Hospital excited because of '000'," Clinical trials of Dream Anticancer Drug without side effects with Kael & GemVax, 4 pages, Apr. 22, 2013.

(56) References Cited

OTHER PUBLICATIONS

Gong, W., et al., "Invasion Potential of H22 Hepatocarcinoma Cells is Increased by HMGB1-induced Tumor NF-kB Signaling via Initiation of HSP70," Oncology Reports 30(3):1249-1256, D.A. Spandidos, Greece (2013).
Guo, R.F., et al., "Regulatory Effects of Eotaxin on Acute Lung Inflammatory Injury," Journal of Immunology 166(8):5208-5218, American Association of Immunologists, United States (2001).
Kawasaki, H., et al, "Detection and Evaluation of Activation of Various Cancer Antigenic Peptide-specific CTLs in Mature Dendritic Cells Used for Dendritic Cell Therapy," The 21st International Congress of Personalized Medicine, Conference Program and Abstracts, Personalized Medicine Universe (Japanese edition) 4(Supplement 2): 2 pages, Oct. 17, 2015.
Morishita, M., and Peppas, N.A., "Is the Oral Route Possible for Peptide and Protein Drug Delivery?," Drug Discovery Today 11(19-20):905-910, Elsevier Science Ltd., England (2006).
Co-pending Application, U.S. Appl. No. 15/479,746, inventors Kim, S.J., et al., filed Apr. 5, 2017 (Not Published).
ClinicalTrials.gov, "Adjuvant Leuprolide with or without Docetaxel in High Risk Prostate Cancer After Radial Prostatectomy," Identifier NCT00283062, first received on Jan. 26, 2006, accessed at https://clinicaltrials.gov/ct2/show/study/NCT00283062, last accessed on May 12, 2017, 7 pages.
ClinicalTrials.gov, "Gemcitabine, Capecitabine, and Telomerase Peptide Vaccine GV1001 in Treating Patients With Locally Advanced and Metastatic Pancreatic Cancer,"Identifier NCT00425360, accessed at https://clinicaltrials.gov/archive/NCT00425360/2007_01_22, last accessed on Apr. 7, 2017, 4 pages.
Kyte, J.A., et al., "Telomerase Peptide Vaccination Combined with Temozolomide: A Clinical Trial in Stage IV Melanoma Patients," Clinical Cancer Research 17(13):4568-4580, The American Association of Cancer Research, United States (2011).
Mandal, A., "Types of Fibrosis," news-medical.net, accessed at http://www.news-medical.net/health/Types-of-Fibrosis.aspx, last accessed on Jul. 3, 2014, 3 pages.
Middleton, G., et al., "Gemcitabine and Capecitabine With or Without Telomerase Peptide Vaccine GV1001 in Patients With Locally Advanced or Metastatic Pancreatic Cancer (TeloVac): an Open-label, Randomised, Phase 3 Trial," The Lancet. Oncology 15(8):829-840, Lancet Pub. Group, England (Jul. 2014).
Nawroth, I., et al., "Intraperitoneal Administration of Chitosan/DsiRNA Nanoparticles Targeting TNFα Prevents Radiation-induced Fibrosis," Radiotherapy and Oncology 97(1):143-148, Elsevier Ireland Ltd., Ireland (2010).
Rosenbloom, J., et al., "Strategies for Anti-fibrotic Therapies" Biochimica et Biophysica Acta 1832(7):1088-1103, Elsevier B.V., Netherlands (2013).
Tisdale, M.J., "Catabolic Mediators of Cancer Cachexia," Current Opinion in Supportive and Palliative Care, 2(4):256-261, Lippincott Williams & Wilkins, United States (2008).
Wynn, T.A. and Ramalingam, T.R., "Mechanisms of Fibrosis: Therapeutic Translation for Fibrotic Disease," Nature Medicine 18(7):1028-1040, Nature Publishing Company, United States (2012).
Albini, A., et al., "Cancer Prevention by Targeting Angiogenesis," Nature reviews Clinical oncology 9(9):498-509, Nature Pub Group (2012).
Auerbach, R., et al., "Angiogenesis Assays: Problems and Pitfalls," Cancer Metastasis Reviews 19(1-2):167-172, Kluwer Academic, Netherlands (2000).
Berendsen, H.J., "A Glimpse of the Holy Grail?," Science 282(5389):642-643, American Association for the Advancement of Science, United States (1998).
De Araujo, J.G., et al., "The Potential Use of Melatonin for Preventing Cisplatin Ototoxicity: An Insight for a Clinical Approach," Advances in Otolaryngology 2014:8 pages, Hindawi Publishing Corporation (2014).
Delves, P.J., "Allergic Rhinitis," Merck manual, accessed at http://www.merckmanuals.com/professional/immunology-allergic-disorders/allergic,-autoimmune,-and-other-hypersensitivity-disorders/allergic-rhinitis, accessed on Nov. 2, 2017, pp. 1-6.
Du, C., et al., "Conformational and Topological Requirements of Cell-permeable Peptide Function," The Journal of Peptide Research 51(3):235-243, Munksgaard, Denmark (1998).
Extended European Search Report for Application No. EP14808179, dated May 24, 2017, 24 pages.
Fauce, S.R., et al., "Telomerase-Based Pharmacologic Enhancement of Antiviral function of Human CD8+ T Lymphocytes, "Immunology 181(10):7400-7406, American Association of Immunologists, United States (Nov. 2008).
Fontanes, V., et al., "A cell permeable peptide inhibits Hepatitis C Virus Replication by Sequestering IRES Transacting Factors," Virology 394(1):82-90, Academic Press, United States (Nov. 2009).
Fred, M.P., "Nonallergic Rhinitis," Merck manual, accessed at http://www.msdmanuals.com/professional/ear,-nose,-and-throat-disorders/nose-and-paranasal-sinus-disorders/nonallergic-rhinitis, accessed on Nov. 2, 2017, pp. 1-3.
International Preliminary Report on Patentability and Written Opinion for International Application No. PCT/KR2015/014099, The International Bureau of WIPO, dated Jun. 27, 2017, 16 pages.
International Preliminary Report on Patentability and Written Opinion for International Application No. PCT/KR2016/001646, Korean Intellectual Property Office, Republic of Korea, dated May 20, 2016, 13 pages.
International Search Report for Application No. PCT/KR2016/007192, dated Sep. 12, 2016, 12 pages.
International Search Report for International Application No. PCT/KR2015/014099, Korean Intellectual Property Office, Republic of Korea, dated May 4, 2016, 8 pages.
International Search Report for International Application No. PCT/KR2016/001646, Korean Intellectual Property Office, Republic of Korea, dated May 20, 2016, 8 pages.
Jain, R.K., "Barriers to Drug Delivery in Solid Tumors," Scientific American 271(1):58-65, Scientific American, Inc., United States (Jul. 1994).
Kalnins, A., et al., "Sequence of the Lacz Gene of *Escherichia coli*," The EMBO Journal 2(4):593-597, Wiley Blackwell, England (1983).
Kim, B.H., "Presbycusis: Review for its Environmental Risk Factors," Korean Journal of Otorhinolaryngology-Head and Neck Surgery 49(10):962-967, Korean Society of Otolaryngology-Head and Neck Surgery, Korea (2006).
Kim, H., et al., "Inhibition of HIV-1 Reactivation by a Telomerase-Derived Peptide in a HSP90-Dependent Manner," Scientific Reports 6: 28896, Nature Publishing Group, England (Jul. 2016).
Lee, E.K., et al., "Inhibition of Experimental Choroidal Neovascularization by Telomerase-derived Peptide GV1001," Investigative Ophthalmology & Visual Science 56(7):Abstract 2291, ARVO Annual Meeting Abstract (Jun. 2015).
Lee, S.A., et al., "A Telomerase-Derived Peptide Regulates Reactive Oxygen Species and Hepatitis C Virus RNA Replication in HCV-Infected Cells via Heat Shock Protein 90," Biochemical and Biophysical Research Communications 471(1):156-162, Elsevier, United States (Feb. 2016).
Leem G., et al., "Immunotherapy in Pancreatic Cancer; the Road Less Traveled," Immunol Disord Immunotherapy, Jun. 26, 2016 (Jun. 26, 2016), p. 1000106, XP055328627, Retrieved from the Internet: (URL:http://www.omicsgroup.orgjjournalsjimmunotherapy-in-pancreatic-cancer-the-road-less-traveled-IDIT-1000104.pdf).
Merck Manual: Respiratory Diseases, Medical Topics, accessed on Nov. 2, 2017, pp. 1-4.
Merck, "Obesity, The Merck Manual Professional Edition," accessed at https://www.merckmanuals.com/professional/nutritional-disorders/obesity-and-the-metabolic-syndrome/obesity, accessed on Oct. 6, 2014, 9 pages.
Middleton, G.W., "A Phase III Randomized Trial of Chemoimmunotherapy Comprising Gemcitabine and Capecitabine with or Without Telomerase Vaccine GV1001 in Patients with Locally Advanced or Metastatic Pancreatic Cancer," Presented at conference ASCO, (Jun. 4, 2013), XP054977010. Retrieved from the Internet: (URL:http://meetinglibrary.asco.orgjcontent/82894?media=vm).

(56) References Cited

OTHER PUBLICATIONS

Middleton, G.W., et al., Phase III Randomized Trial of Chemoimmunotherapy Comprising Gemcitabine and Capecitabine with or without Telomerase Vaccine GV1001 in Patients with Locally Advanced or Metastatic Pancreatic Cancer, ASCO Annual Meeting, 31:1-3, (May 31, 2013)-(Jun. 4, 2013), XP055328310.

Middleton, G.W., et al., Poster: Predictive Cytokine Biomarkers for Survival in Patients with Advanced Pancreatic Cancer Randomized to Sequential Chemoimmunotherapy Comprising Gemcitabine and Capecitabine (GemCap) Followed by the Telomerase Vaccine GV1001 Compared to Concurrent Chemoimmunotherapy in the Telovac Phase III tr, ASCO 2014, May 30, 2014 (May 30, 2014)-Jun. 3, 2014 (Jun. 3, 2014), pp. 1-1. XP055328448. Retrieved from the Internet: (URL:http://media4.asco.org/144/8599/93976/93976_poster_pvhr.jpg).

Neoptolemos J.P., et al., "Predictive 1-20 Cytokine Biomarkers for Survival in Patients With Advanced Pancreatic Cancer Randomized to Sequential Chemoimmunotherapy Comprising Gemcitabine and Capecitabine (Gemcap) Followed by the Telomerase Vaccine GV1001 Compared to Concurrent Chemoimmunotherapy in the Telovac Phase III trial," 2014 ASCO Annual Meeting, May 30, 2014 (May 30, 2014)-Jun. 3, 2014 (Jun. 3, 2014), pp. 1-3.

Ngo. et al., "Computational Complexity, Protein Structure Prediction, and the Levinthal Paradox," in the Protein Folding Problem and Tertiary Structure Prediction, Merz, Jr., K.M., and Le Grand, S.M., eds., pp. 491-494, Birkhauser Boston, United States (1994).

O'Beirne, J., et al., "Generation of Functional CD8+ T Cells by Human Dendritic Cells Expressing Glypican-3 Epitopes," in: Journal of Experimental and Clinical Cancer Research 29:48, BioMed Central, London (May 2010).

Ortega, V.E., "Asthma," Merck manual, accessed at http://www.merckmanuals.com/professional/pulmonary-disorders/asthma-and-related-disorders/asthma, accessed on Nov. 2, 2017, pp. 1-19.

Priya, S.G., et al., "Skin Tissue Engineering for Tissue Repair and Regeneration," Tissue Engineering. Part B, Reviews 14(1):105-118, Mary Ann Liebert, Inc., United States (2005).

Rosenstein, B.J., "Cystic Fibrosis," Merck manual, accessed at http://www.msdmanuals.com/professional/pediatrics/cystic-fibrosis-cf/cystic-fibrosis, accessed on Nov. 2, 2017, pp. 1-15.

Rowe-Rendleman, C. and Glickman, R.D., "Possible therapy for age-related macular degeneration using human telomerase," Brain Research Bulletin 62(6):549-553, Elsevier Science Inc., United States (2004).

Rudinger, J., "Characteristics of the Amino Acids as Components of a Peptide Hormone Sequence," in Peptide Hormones, Parsons, J.A., ed., University Park Press, United States (1976).

Schwarze, S.R., et al., "In Vivo Protein Transduction: Delivery of a Biologically Active Protein Into the Mouse," Science 285(5433):1569-1572, American Association for the Advancement of Science, United States (1999).

SIGMA Genosys, "Designing Custom Peptides," accessed at http://www.sigma-genosys.com/peptide_design.asp, Accessed on Dec. 16, 2004, 2 pages.

Supplemental European Search Report for Application No. EP14808179, dated Jan. 10, 2017, 13 pages.

Varma, N., et al., "Role of hTERT and WT1 Gene Expression in Disease Progression and Imatinib Responsiveness of Patients with BCR-ABL Positive Chronic Myeloid Leukemia," in: Leukemia and Lymphoma 52(4):687-693, Informa Healthcare, London (Ap. 2011).

Voet, D. and Voet, J.G., "Abnormal Hemoglobins," in Biochemistry, 2nd Edition, Chapter 9, pp. 235-241, John Wiley & Sons, Inc., United States (1995).

Westin, E.R., et al., "The p53/p21(WAF/CIP) Pathway Mediates Oxidative Stress and Senescence in Dyskeratosis Congenita Cells With Telomerase Insufficiency," Antioxidants & Redox Signaling 14(6):985-997, Mary Ann Liebert, Inc., United States (2011).

Written opinion for Application No. PCT/KR2016/007192, dated Sep. 12, 2016, 16 pages.

Co-pending Application, U.S. Appl. No. 15/772,928, inventors Kim, S.J., et al., filed Nov. 3, 2016 (Not Published).

International Search Report and Written Opinion for International Application No. PCT/KR2016/012613, Korean intellectual Property Office, Republic of Korea, dated Feb. 2, 2017, 14 pages.

Kirino, T, "Delayed Neuronal Death in the Gerbil Hippocampus Following Ischemia," Brain Research 239(1):57-69, Amsterdam Elsevier/North-Holland Biomedical Press, Netherlands (May 1982).

Olney, J.W., et al., "Pathological Changes Induced in Cerebrocortical Neurons by Phencyclidine and Related Drugs," Science 244(4910):1360-1362, American Association for the Advancement of Science, United States (Jun. 1989).

Hey, Y.Y and O'Neill, H.C., "Murine spleen contains a diversity of myeloid and dendritic cells distinct in antigen presenting function," Journal of Cellular and Molecular Medicine, 16(11):2611-2619, Wiley-Blackwell, England (Nov. 2012).

Tarantino, G., et al. "Spleen: a New Role for an Old Player?," World Journal of Gastroenterology, 17(33):3776-3784, Baishideng Publishing Group, United States (Sep. 2011).

Petrylak D.P., "The Treatment of Hormone-Refractory Prostate Cancer: Docetaxel and Beyond," Reviews in Urology 8 (Suppl 2): S48-S55, United States (2006).

Shay, J.W., and Keith, W.N., "Targeting Telomerase for Cancer Therapeutics," in: British Journal of Cancer 98(4):677-683, Nature Publishing Group on behalf of Cancer Research UK (2008).

\* cited by examiner

METHOD OF MODULATING SEX HORMONE LEVELS USING A SEX HORMONE SECRETION MODULATOR

REFERENCE TO SEQUENCE LISTING SUBMITTED ELECTRONICALLY VIA EFS-WEB

The content of the electronically submitted sequence listing (Name: 2473_0860001_SeqListing.txt; 2,875 bytes; and Date of Creation: Aug. 14, 2017) is herein incorporated by reference in its entirety.

BACKGROUND

1. Field

One or more embodiments of the present invention relate to a hormone secretion modulator including a peptide derived from telomerase, more particularly, a peptide comprising an amino acid sequence of SEQ ID NO: 1, an amino acid sequence having a sequence identity of at least 80% with SEQ ID NO: 1, or a peptide fragment thereof, a pharmaceutical composition comprising the hormone secretion modulator, and a use of the pharmaceutical composition for treatment, alleviation, or prevention of diseases caused by excessive or deficient levels of hormones.

2. Description of the Related Art

Hormones related to generation, development, and aging of reproductive organs of humans are called sex hormones, and representative examples of the sex hormones include testosterone, estrogen, follicle-stimulating hormone (FSH), luteinizing hormone (LH), and gonadotropin-releasing hormone (GnRH).

Testosterone is one of the primary sex hormones produced in the bodies of both males and females. Testosterone is primarily produced in interstitial cells (Leydig cells) of testicles in males and in the ovaries and placenta in females. Also, testosterone is produced in adrenal cortex in both males and females. One of the primary roles of testosterone is the development of secondary sexual characteristics, for example, increasing masses of muscles, bones, and bodily hair.

LH is a glycoprotein hormone comprised of two subunits. Alpha subunits of LH are similar to those of FSH, human chorionic gonadotropin (hCG), and thyroid-stimulating hormone (TSH). Beta subunits of LH are different from those of other glycoprotein hormones and provide biochemical specificity to LH. LH is secreted from anterior pituitary, and in males, LH is secreted after reacting with GnRH secreted from hypothalamus. LH is also known as interstitial-cell-stimulating hormone (ICSH) and the secretion of LH is regulated by a balance of positive and negative feedback mechanisms including a hypothalamic-pituitary axis, reproductive organs, a pituitary gland, and sexual steroid hormones. LH and the other pituitary gonadotropin and FSH, play a critical role in maintaining the normal function of the male and female reproductive systems.

FSH is a glycoprotein hormone comprised of two subunits. Alpha subunits of FSH are similar to those of LH, hCG, and TSH. Beta subunits of FSH are different from those of other glycoprotein hormones and confer biochemical specificity. FSH is secreted from anterior pituitary in response to GnRH secreted from hypothalamus. In both males and females, FSH secretion is regulated by a balance of positive and negative feedback mechanisms involving the hypothalamicpituitary axis, the reproductive organs, and the pituitary and sex steroid hormones. FSH and LH and the other pituitary gonadotropin play a critical role in maintaining the normal function of the male and female reproductive systems.

Estrogen is a female steroid hormone, which is mostly produced in the ovaries, and a small amount of estrogen is produced in adrenal cortex, placenta, and male testes. Estrogen helps control and guide sexual growth including physical changes associated with puberty. It also influences the course of ovulation in the monthly menstrual cycle, lactation after pregnancy, aspects of mood, and the aging process. Production of estrogen changes naturally over the female lifespan, reaching adult levels with the onset of puberty (menarche) and decreasing in middle age until the onset of menopause. Estrogen deficiency can lead to lack of menstruation (amenorrhea), persistent difficulties associated with menopause (such as mood swings and vaginal dryness), and osteoporosis in older age. In cases of estrogen deficiency, natural and synthetic estrogen preparations may be prescribed. Estrogen is also a component of many oral contraceptives. An overabundance of estrogen in men causes development of female secondary sexual characteristics (feminization), such as enlargement of breast tissue.

The gonadotropin-releasing hormones (GnRH) (gonadoliberin) are a family of peptides that play a pivotal role in reproduction. The main function of GnRH is to act on the pituitary to stimulate the synthesis and secretion of luteinizing and follicle-stimulating hormones, but GnRH also acts on the brain, retina, sympathetic nervous system, gonads, and placenta in certain species. There seems to be at least three forms of GnRH. The second form is expressed in midbrain and seems to be widespread. The third form has been found so far only in fish. GnRH is a C-terminal amidated decapeptide processed from a larger precursor protein. Four of the ten residues are perfectly conserved in all species where GnRH has been sequenced.

PRIOR ART

Patents

US 20020042401 A1
US 20120277290 A1

Non-Patents

Christoph Eisenegger et al., Trends in Cognitive Sciences June 2011, Vol. 15, No. 6.

SUMMARY

According to one or more embodiments of the present invention, provided is a hormone secretion modulator comprising a peptide including an amino acid sequence of SEQ ID NO: 1, an amino acid sequence having a sequence identity of at least 80% with SEQ ID NO: 1, or a peptide fragment thereof.

According to other embodiments of the present invention, provided is a pharmaceutical composition for modulating hormone secretion including a hormone secretion modulator according to an embodiment of the present invention.

According to other embodiments of the present invention, provided is a use of a hormone secretion modulator for preparing a medicament for modulating hormone secretion.

According to other embodiments of the present invention, provided is a kit for hormone secretion modulation including a pharmaceutical composition according to an embodiment; and a package insert.

According to other embodiments of the present invention, provided is a method of modulating hormone levels, the method including administration of an effective amount of a hormone secretion modulator according to an embodiment to a subject in need of a hormone modulation treatment.

According to other embodiments of the present invention, provided is a method of modulating hormone levels, the method including administration of an effective amount of a pharmaceutical composition for modulating hormone secretion to a subject in need of a hormone modulation treatment.

According to other embodiments of the present invention, provided is a GnRH analog comprising a peptide including an amino acid sequence of SEQ ID NO: 1, an amino acid sequence having a sequence identity of at least 80% with SEQ ID NO: 1, or a peptide fragment thereof.

According to other embodiments of the present invention, provided is a method of modulating effects of gonadotropin releasing hormone (GnRH), the method including administration of an effective amount of GnRH analog according to an embodiment to a subject in need of a hormone modulation treatment.

According to other embodiments of the present invention, provided is a pharmaceutical composition for modulating effects of GnRH, the pharmaceutical composition including a GnRH analog according to an embodiment.

According to other embodiments of the present invention, provided is a use of GnRH analog according to an embodiment of the present invention for preparing a medicament for modulating effects of GnRH.

INDUSTRIAL APPLICABILITY

A hormone secretion regulator according to an embodiment of the present invention was shown to have no or insignificant side effects. Accordingly, the hormone secretion regulator according to an embodiment of the present invention may be used as a GnRH analog for 1) an anti-cancer treatment of hormone sensitive cancer, such as prostate cancer or breast cancer, 2) treatment of the disruption of estrogen production in females, such as menorrhagia, endometriosis, uterine fibroids, and uterine fibrotic cysts, 3) treatment of infertility in females and males, 4) treatment of precocious puberty in children, and 5) treatment and alleviation of benign prostatic hyperplasia.

DETAILED DESCRIPTION

Figure 1:
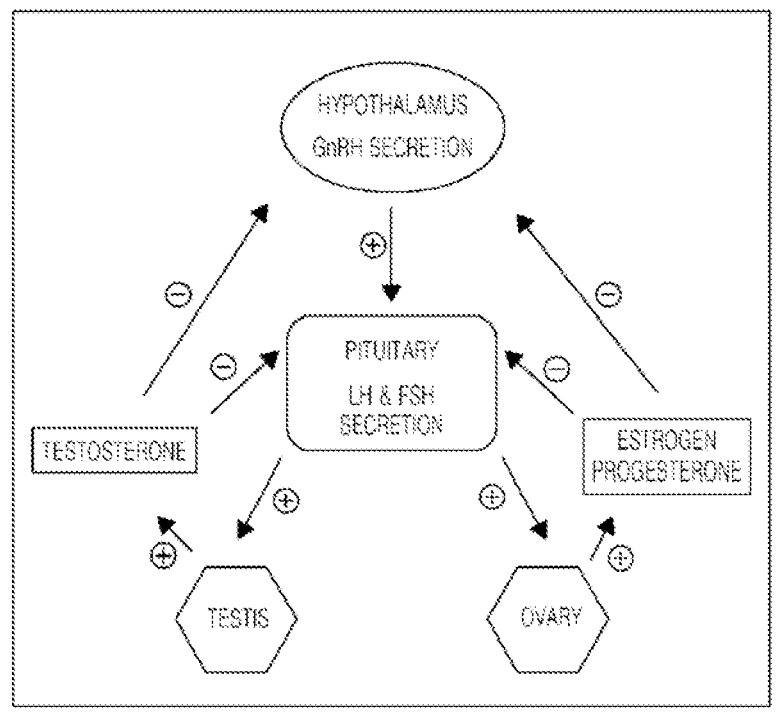
FIG. 1 is a graph showing hormone modulation loop of testosterone, estrogen, FSH, LH and GnRH in reproductive organs of males and females.

Since the present invention can be adapted to various fields of use and in various modifications, below is a more detailed description of the present invention. Nevertheless, this is no means to limit the form of practical application; it should be understood that the intention is to include the concept and the extent of technology in all of the modifications, equivalents to alternatives. In describing the present invention, if any detailed description about the prior art is considered to deteriorate the fundamental principles of the present invention, the description will be omitted.

According to an embodiment of the present invention, provided is a peptide for modulation of hormone secretion, the peptide comprising an amino acid sequence of SEQ ID NO: 1, an amino acid sequence having a sequence identity of at least 80% with SEQ ID NO: 1, or a fragment peptide thereof.

The peptides disclosed herein may include a peptide comprising an amino acid sequence identity of above 80%, above 85%, above 90%, above 95%, above 96%, above 97%, above 98%, or above 99%. Moreover, the peptides disclosed in the present invention may include a peptide comprising SEQ ID NO: 1 or its fragments, and a peptide with more than 1 transformed/substituted amino acid, more than 2 transformed/substituted amino acids, more than 3 transformed/substituted amino acids, more than 4 transformed/substituted amino acids, more than 5 transformed/substituted amino acids, more than 6 transformed/substituted aminos acid, or more than 7 transformed/substituted amino acids.

As used herein, the expressions "homology" and "sequence identity" may be interchangeably used to indicate the overlap between two amino acids (or similarly, nucleic acids) in a sequence.

Unless a different term is used for "sequence identity" of a peptide or a nucleic acid, the sequence identity is calculated by using (nref−ndif)*100/nref, wherein when two sequences are aligned to obtain the greatest number of matches, ndif represents a total number of non-identical residues between the two sequences and nref represents a total number of residues of a shorter sequence among the two sequences. For example, a sequence identity between agtcagtc and aatcaatc calculated from the formula above is 75% (nref=8, ndif=2).

According to an aspect of the present invention, the sequence identity was determined by conventional methods described below. Smith and Waterman, 1981, Adv. Appl. Math. 2:482, by the search for similarity method of Pearson & Lipman, 1988, Proc. Natl. Acad. Sci. USA 85:2444, using the CLUSTAL W algorithm of Thompson et al., 1994, Nucleic Acids Res 22:467380, by computerized implementations of these algorithms (GAP, BESTFIT, FASTA, and TFASTA in the Wisconsin Genetics Software Package, Genetics Computer Group). The BLAST algorithm (Altschul et al., 1990, Mol. Biol. 215:403-10) for which software may be obtained through the National Center for Biotechnology Information (www.ncbi.nlm.nih.gov/) may also be used. When using any of the aforementioned algorithms, the default parameters for "Window" length, gap penalty, etc.

According to an embodiment of the present invention, changes in an amino acid sequence belong to the modification of peptide's physical and chemical characteristics. For example, amino acid transformation can be performed by improving the thermal stability of the peptide, altering substrate specificity, and changing the optimal pH.

Also, the peptide comprising the amino acid sequence of SEQ ID NO: 1, the amino acid sequence having a sequence identity of at least 80% with SEQ ID NO: 1, or the fragment thereof have low toxicity in cells and thus, have high in vivo safety.

SEQ ID NO: 1: EARPALLTSRLRFIPK

According to another embodiment of the present invention, provided is a hormone secretion modulator including a peptide, which includes an amino acid sequence of SEQ ID NO: 1, an amino acid sequence having a sequence identity of at least 80% with SEQ ID NO: 1, or a fragment thereof.

According to an embodiment of the present invention, the hormone is a sexual hormone, which may be selected from the group consisting of testosterone, estrogen, FSH, LH, GnRH, and a combination thereof.

According to an embodiment of the present invention, the hormone is testosterone.

Testosterone (4-androstene-17β-ol-3-one) is a C19 steroid hormone, which is an important androgen for males. Testosterone is modulated by LH, which is a pituitary gland hormone. LH is secreted from an anterior pituitary gland and directly acts on interstitial cells of testicles to modulate the production of testosterone. Testosterone stimulates the maturation of external reproductive organs, the development of secondary sexual characteristics, and the growth of hair on the face, armpits, and genital regions.

In the circulatory system, measuring the levels of LH and testosterone are useful for the identification of hypogonadism. Low concentrations of testosterone are caused by hypogonadism, testicular dysfunction, elevated prolactin levels, pituitary dysfunction, and kidney or liver diseases. Females have much lower levels of testosterone than males and high levels of testosterone in females may cause polycystic ovary syndrome and adrenal hyperplasia. Excessive testosterone may cause infertility, hirsutism, amenorrhea, or obesity.

Testosterone binds strongly to plasma proteins such as sex hormone-binding globulins (SHBG) and testosterone-estradiol-binding globulins (TeBG) and binds weakly to cortisol-binding globulins (CBG) and albumin. Only less than 2.5% of testosterone circulates freely in the body.

In an embodiment of the present invention, the hormone is estrogen, which may be estrone (E1), estradiol (E2), or estriol (E3).

Three primary estrogens naturally produced in females are estrone (E1), estradiol (E2), and estriol (E3). Estradiol is the predominant estrogen during reproductive years both in terms of absolute serum levels as well as in terms of estrogenic activity. Measurement of Estradiol (E2) is used to evaluate ovarian function and has an important use in monitoring the development of follicle in Assisted Reproduction Protocol. E2 promotes growth of female reproductive organs, stimulates secondary sexual characterization, as well as having an essential role in the menstrual cycle. Usually in females who are not pregnant, estradiol is mostly secreted by the interaction between theca and granulose cells during the development of follicle and corpus luteum. During pregnancy, placenta becomes the major site of estradiol secretion. Within the estradiol secreted in the blood, 1~3% exists freely without binding to any proteins, about 40% exists in a form bound to globulin (SHBG), and the rest exists in a form bound to albumin. Estradiol's primary function is to stimulate the growth of female reproductive organs and to develop secondary sexual characteristics.

Estradiol (E2) is necessary in female menstrual cycles. In the beginning of production of follicles, estradiol (E2) is maintained at a low level. After about 7 days, the maturation of follicles is modulated by the level of estradiol (E2), and the level of estradiol (E2) increases. An increased level of estradiol (E2) induces a sharp increase in the level of LH and a suppressed level of FSH. A normal ovulation occurs after about 10 hours to about 12 hours after the peak of the level of LH and about 24 hours to about 36 hours after the peak level of estradiol (E2). During a luteal phase, the estradiol (E2) level increases and reaches its peak (the maximum level) 8 days after ovulation. Such an increase in the level of estradiol (E2) represents regression of corpus luteum. When a fertilized egg is not implanted, the level of estradiol (E2) decreases, which acts as a signal for the start of a next phase.

The name 'estradiol-6 test' is derived from an antibody-antigen response that occurs at a sixth binding site of estradiol (E2), which shows good test specificity, and results of the test may be used in various ways.

According to an embodiment of the present invention, the hormone is FSH. FSH is a glycoprotein hormone composed of α-subunit similar to LH, TSH, hCG and β-subunit which expresses FSH's biochemical characteristics, and along with LH, has an important role in maintaining the normal functions of reproductive systems in both males and females. FSH is released from anterior pituitary gland stimulated by gonadotropin-releasing hormone (GnRH) secreted by hypothalamus. In both males and females, FSH maintains homeostasis by feedback mechanisms related to hypothalamus-pituitary pathway, reproductive organs, pituitary gland, sex hormones, etc.

Sites of action of FSH are as shown below in males and females, respectively.

TABLE 1

| Sex | Site of action | Action |
|---|---|---|
| Female | Ovarian follicles | Stimulation of production of estradiol and estrogen and follicular development during a menstrual cycle<br>Stimulation of ovulation with LH |
| Male | Sertolli cells (in seminiferous tubules of testes) | Stimulation of spermatogenesis |

An increased level of FSH represents menopause in females and primary hypogonadism in males and females. A decreased level of FSH is related to primary hypogonadism. In females suffering from polycystic ovary syndrome, the level of FSH is normal or decreased.

In an embodiment of the present invention, the hormone is LH.

Luteinizing Hormone (LH) is a glycoprotein hormone with two subunits. It is composed of α-subunit similar to FSH, TSH, hCG and β-subunit which expresses LH's biochemical characteristics which are different than other glycoprotein hormones. LH is released from anterior pituitary gland stimulated by gonadotropin-releasing hormone (GnRH) secreted by hypothalamus. In males, LH is sometimes called interstitial cell stimulating hormone (ICSH). In both males and females, LH levels are controlled by feedback mechanisms related to hypothalamus-pituitary pathway, reproductive organs, pituitary gland, sex hormones, etc. LH, as well as pituitary gonadotropin and FSH among others, have very important roles in male and female reproductive systems.

Targets of LH in males and females and functions thereof are shown in Table 2 below.

TABLE 2

| Sex | Site of action | Action |
|---|---|---|
| Female | Follicular cells of ovarian follicles | Stimulates the production of androgen that mediates transformation of FSH into estradiol during follicular maturation |
|  | Graafian follicle | Stimulates ovulation with FSH during an intermediate phase |
|  | Corpus luteum | Stimulates the production of corpus luteum after ovulation and secretion of progesterone |
| Male | Interstitial tissue cells of seminiferous tubules of testes | Stimulates secretion of testosterone |

An abnormal level of LH is related to increased levels of FSH, estrogen, and progesterone. An increased concentration of LH indicates menopause, polycystic ovary syndrome, and primary hypogonadism in females, and primary hypogonadism in males. On the other hand, a decreased concentration of LH indicates primary hypergonadism.

According to an embodiment of the present invention, the hormone is GnRH.

The peptide comprising the amino acid sequence of SEQ ID NO: 1, the amino acid sequence having a sequence identity of at least 80% with SEQ ID NO: 1, or the fragment thereof may act as a GnRH analog, and the GnRH analog may act as a GnRH agonist or a GnRH antagonist.

The GnRH analog may be used to treat steroid-related diseases (for example: prostate cancer, breast cancer, and ovarian cancer) and diseases associated with the hypofunction of reproductive endocrinology (ex: irregular menstruation, amenorrhea, precocious puberty, and hypogonadism), the control of ovulation periods in in vitro fertilization (ex: the ovulation periods can be optionally controlled by administering GnRH agonists or antagonists), for contraception (for example: the growth and implantation rate of a fetus may be blocked or reduced due to the administration of a GnRH antagonist after a sexual intercourse), or for increased production of fish and livestock. Accordingly, potential use of the present invention in the field of medicine may be achieved by using the GnRH analog, which may be used for modulating the effects of GnRH. Such modulation of the effects of GnRH includes an increase or a decrease in the effects of GnRH, and the modulation may be used as 1) an anti-cancer treatment of hormone sensitive cancer, such as prostate cancer and breast cancer, 2) treatment of the disruption of estrogen production in females, such as menorrhagia, endometriosis, uterine fibroids, and uterine fibrotic cysts, 3) treatment of infertility in females and males, 4) treatment of precocious puberty in children, and 5) treatment and alleviation of benign prostatic hyperplasia.

Accordingly, provided is a GnRH analog including a peptide, which includes an amino acid sequence of SEQ ID NO: 1, an amino acid sequence having a sequence identity of at least 80% with SEQ ID NO: 1, or a fragment thereof.

According to another embodiment of the present invention, provided is a composition for hormone secretion modulation, the composition including a hormone secretion modulator according to an embodiment of the present invention.

According to another embodiment of the present invention, provided is a pharmaceutical composition for modulating hormone secretion including a hormone secretion modulator and a pharmaceutically acceptable additive.

According to another embodiment of the present invention, provided is a pharmaceutical composition for modulating the effects of GnRH, the pharmaceutical composition including a GnRH analog according to an embodiment of the present invention.

According to an embodiment of the present invention, the composition may contain about 0.1 μg/mg to about 1 mg/mg, specifically about 1 μg/mg to about 0.5 mg/mg, more specifically about 10 μg/mg to about 0.1 mg/mg of a peptide comprising an amino acid sequence of SEQ ID NO: 1, an amino acid sequence having a sequence identity of at least 80% with SEQ ID NO: 1, or a fragment thereof. When the peptide is contained in the above-mentioned range, both the safety and stability of the composition may be appropriate and satisfied in the aspect of cost-effectiveness.

According to an embodiment of the present invention, the composition may have applications to all animals including humans, dogs, chickens, pigs, cows, sheep, guinea pigs, and monkeys.

According to an embodiment of the present invention, the pharmaceutical composition may include a peptide composed of an amino acid sequence of SEQ ID NO: 1, a peptide having a sequence identity of at least 80% with SEQ ID NO: 1, or a fragment peptide thereof as an active component.

According to an embodiment of the present invention, a pharmaceutical composition may be administered through oral, rectal, transdermal, intravenous, intramuscular, intraperitoneal, intramedullary, epidural, or subcutaneous means.

The hormone secretion modulator according to an embodiment of the present invention may act as the GnRH analog, and the pharmaceutical composition including the hormone secretion modulator is particularly useful for the treatment of a subject (human or others) having diseases or symptoms related to hormone levels inducing symptoms of diseases disclosed herein or hormone levels that affect diseases or progression of the diseases. Accordingly, the pharmaceutical composition according to an embodiment of the present invention may be used for treatment, alleviation, or prevention of diseases caused by hormones, more particularly excessive or deficient levels of sex hormones. According to an embodiment of the present invention, the diseases caused by excessive or deficient levels of hormones may be selected from prostate cancer, breast cancer, ovarian cancer, menorrhagia, endometriosis, adenomyosis, uterine fibroid, female or male infertility, precocious puberty in children, prostatic hypertrophy, or a combination thereof, but the diseases are not limited thereto. The pharmaceutical composition may be formulated into a conventional pharmaceutical formulation known in the art. The pharmaceutical composition may be administered as any formulation for oral administration, injection, suppository, dermal administration, and nasal administration, but the pharmaceutical composition is not limited thereto and may preferably formulated as a formulation for oral administration.

Formulations of oral administration may be, but not limited to, tablets, pills, soft or hard capsules, granules, powders, solutions, or emulsions. Formulations of non-oral administration may be, but not limited to, injections, drips, lotions, ointments, gels, creams, suspensions, emulsions, suppositories, patches, or sprays.

According to an embodiment of the present invention, the pharmaceutical composition, if necessary, may contain additives, such as diluents, excipients, lubricants, binders, disintegrants, buffers, dispersants, surfactants, coloring agents, aromatics, or sweeteners. According to an embodiment of the present invention, the pharmaceutical composition may be prepared by conventional methods known in the art.

According to an embodiment of the present invention, the active component of the pharmaceutical composition may vary according to the patient's age, sex, weight, pathology state and severity, administration route, or a prescriber's judgment. Dosage may be determined by one of ordinary skill in the art based on the above-mentioned factors, and the daily dose may be, but is not limited to, about 0.1 μg/kg/day to about 1 g/kg/day, specifically about 1 μg/kg/day to about 10 mg/kg/day, more specifically about 10 μg/kg/day to about 1 mg/kg/day, and more specifically about 50 μg/kg/day to about 100 μg/kg/day. According to an embodiment of the present invention, the pharmaceutical composition may be administered, but is not limited to, 1 to 3 times a day.

According to another embodiment of the present invention, provided is a food composition for modulating hormone levels. The food composition may include a peptide comprising an amino acid sequence of SEQ ID NO: 1, an amino acid sequence having a sequence identity of at least 80% with SEQ ID NO: 1, or a fragment thereof.

According to an embodiment of the present invention, a food composition is not limited in terms of its formulations, but the food composition may be granules, powder, liquid formulations, or solid preparations. In addition to the active ingredients, each formulation may be prepared with ingredients commonly used in the industry and appropriately chosen by those skilled in the art, and the effects of the formulation may increase when the formulation is applied simultaneously with other ingredients.

Determination of a dosage of the above-mentioned active ingredient may be known by one of ordinary skill in the art, and a daily dosage may be about 0.1 μg/kg/day to about 1 g/kg/day, and more specifically about 1 μg/kg/day to about 10 mg/kg/day, more specifically about 10 μg/kg/day to about 1 mg/kg/day, and more specifically about 50 μg/kg/day to about 100 μg/kg/day. However, the daily dosage is not limited to these numbers and may vary according to other various factors such as age, health status, and complications of the subject of administration.

According to an embodiment, the peptide according to an embodiment of the present invention may be administered in combination with an adjuvant. Accordingly, the composition, the pharmaceutical composition, and the food composition according to an embodiment of the present invention may include an adjuvant. The adjuvant may include any immunological adjuvant known in the art, for example, an inorganic adjuvant, such as aluminum salt and an organic adjuvant, such as an oil-based adjuvant, virosome, or squalene. The organic adjuvant may be an emulsion, a microorganism-derived adjuvant, a synthetic adjuvant, or a cytokine, but it is not limited thereto. 9 types of cytokine adjuvants are known in the art. One example is a granulocyte-macrophage colony-stimulating factor (GM-CSF), which activates mature granulocytes and macrophages and is primarily used as a vaccine for hepatitis B, HIV, and cancer [J Biomed Biotechnol. 2012; 2012: 831486. Published online Mar. 13, 2012].

A suitable dosage of the adjuvant is already known in the art, and thus, the adjuvant may be administered according to the standard known in the art. The determination of a dosage of the adjuvant may be known by one of ordinary skill in the art, and a daily dosage may be about 1 μg/kg/day to about 10 g/kg/day, more specifically about 10 μg/kg/day to about 100 mg/kg/day, and more specifically about 50 μg/kg/day to about 10 mg/kg/day, but the dosage is not limited thereto, and may vary depending on various factors such as age, health status, and complications of the subject of administration. For example, a dosage of about 7 mg to about 700 mg of GM-CSF may be subcutaneously administered at about 1 minute to about 150 minutes before, about 5 minutes to about 80 minutes before, or about 10 minutes to about 15 minutes before the administration of the peptide disclosed herein. The time of administration may be about at least 1 minute before, at least 3 minutes before, at least 5 minutes before, at least 7 minutes before, at least 8 minutes before, at least 9 minutes before, or at least 10 minutes before the administration of the peptide. Also, the time of administration may be administered at least 150 minutes before, at least 130 minutes before, at least 110 minutes before, at least 100 minutes before, at least 90 minutes before, at least 80 minutes before, at least 70 minutes before, at least 60 minutes before, at least 50 minutes before, at least 40 minutes before, at least 30 minutes before, at least 20 minutes before, or at least 15 minutes before the administration of the peptide. The dosage may be about 7 mg or greater, about 10 mg or greater, about 20 mg or greater, about 30 mg or greater, about 40 mg or greater, about 50 mg or greater, about 60 mg or greater, or about 70 mg or greater. Also, the dosage may be about 700 mg or less, about 600 mg or less, about 500 mg or less, about 400 mg or less, about 300 mg or less, about 200 mg or less, about 100 mg or less, about 90 mg or less, or about 80 mg or less.

According to another embodiment of the present invention, provided is a kit for hormone secretion modulation including a pharmaceutical composition according to an embodiment; and a package insert.

The package insert may disclose active components, contents, characteristics, efficacy, dose regimen, storage, usage period, the seller, the manufacturer, date of manufacture, side effects, and/or contraindications of the pharmaceutical composition.

According to another embodiment of the present invention, provided is a use of the hormone secretion modulator according to an embodiment of the present invention for the manufacture of a medicament for modulating hormone secretion Detailed descriptions of the medicament for hormone secretion may be the same as the description of the pharmaceutical composition for modulating hormone secretion according to an embodiment of the present invention.

According to another embodiment of the present invention, provided is a method of modulating hormone levels, the method including administration of an effective amount of a hormone secretion modulator according to an embodiment to a subject in need of a hormone modulation treatment.

According to another embodiment of the present invention, provided is a method of modulating hormone levels, the method including administration of an effective amount of a pharmaceutical composition for modulating hormone secretion to a subject in need of a hormone modulation treatment.

Detailed descriptions of the method of modulating hormone levels may be the same as the description of the hormone secretion modulator and the pharmaceutical composition according to an embodiment of the present invention.

The method of modulating hormone levels includes increasing or decreasing hormone levels for achieving normal hormone levels or for treating, alleviating, or preventing diseases induced by hormones. The method may vary depending on types of disease induced by hormones. The hormones for the method of modulating hormone levels may be selected from the group consisting of testosterone, estrogen, FSH, LH, GnRH, or a combination thereof.

The method of modulating hormone levels may be suitably determined by one of ordinary skill in the art and a method of administering the pharmaceutical composition may be applied to an embodiment of the present invention.

An embodiment of the method of modulating hormone levels may include administration of the hormone secretion modulator or the pharmaceutical composition for modulating hormone secretion once a day.

The method of modulating hormone levels may treat, alleviate, or prevent diseases related to excessive or deficient levels of sex hormones. In an embodiment of the present invention, diseases related to the excessive or deficient levels of sex hormones may be prostate cancer, breast cancer, ovarian cancer, menorrhagia, endometriosis, adenomyosis, uterine fibroid, female or male infertility, precocious puberty in children, prostatic hypertrophy, or a combination thereof, but the diseases are not limited thereto.

According to another embodiment of the present invention, provided is a use of GnRH analogs according to an embodiment for manufacturing a medicament for modulating the effects of GnRH.

The detailed description of the medicament for modulating the effects of GnRH may be the same as the description for the pharmaceutical composition for modulating the effects of GnRH.

According to another embodiment of the present invention, provided is a method of modulating the effects of GnRH, the method including administration of an effective amount of GnRH analog according to an embodiment to a subject in need of a hormone modulation treatment.

The method of modulating the effects of GnRH includes increasing or decreasing hormone levels for achieving normal hormone levels or for treating, alleviating, or preventing diseases induced by hormones. The method may vary depending on types of diseases induced by hormones.

According to an embodiment of the method of modulating the effects of GnRH, the method may include administration of the GnRH analog or a pharmaceutical composition including the GnRH analog once a day.

The method of modulating the effects of GnRH may treat, alleviate, or prevent diseases related to excessive or deficient levels of sex hormones. In an embodiment, the diseases related to excessive or deficient levels of sex hormones may be selected from prostate cancer, breast cancer, ovarian cancer, menorrhagia, endometriosis, adenomyosis, uterine fibroid, female or male infertility, precocious puberty in children, prostatic hypertrophy, or a combination thereof, but the diseases are not limited thereto.

The terms used herein are intended to be used to describe the embodiments and not to limit the present invention. Terms without numbers at the front thereof are not used to limit their quantities but to show that there may be one or more of the objects being referred to by the terms. The terms "including", "having", and "comprising" are interpreted openly (i.e. "including but not limited to").

Ranges of numbers are used instead of stating separate numbers within the ranges; and thus, each number may be integrated herein as separate numbers, unless explicitly stated otherwise. The end values of all ranges are included in the ranges and may be combined independently.

Unless otherwise noted or clearly contradictory in the context, all methods mentioned herein may be performed in a suitable order. The use of any one embodiment, all embodiments, or exemplary language (e.g., that use "like ~") is to clearly describe the present invention, not to limit the scope of the present invention, unless included in the claims. Any language herein outside of the claims should not be interpreted as a necessity of the present invention. Unless defined otherwise, technical and scientific terms used herein have meanings normally understood by a person skilled in the art that the present invention belongs to.

The exemplary embodiments of the present invention are the best mode known to the inventors to perform the present invention. When statements written before the exemplary embodiments are read, modification of the exemplary embodiments may become clear to those skilled in the art. The present inventors hope that those skilled in the art may use the variations adequately and present invention be conducted in other ways than those listed herein. Thus, the present invention, as allowed by the patent law, includes equivalents, and variations thereof, of the key points of the invention stated in the appended claims. In addition, all possible variations within any combination of the above-mentioned components are included in the present invention, unless explicitly stated otherwise or contradicting in context. Although the present invention is described and shown by exemplary embodiments, those skilled in the art will understand well that there can be various changes in the form and details without departing from the spirit of the invention and range, defined by the claims below.

MODE OF THE INVENTION

1. Methods of Synthesis and Analysis of Peptides

Example 1: Synthesis of Peptides

A peptide including SEQ ID NO: 1, a peptide having a sequence identity of 80% or greater to the peptide, or a peptide fragment thereof was prepared according to a solid phase peptide synthesis known in the art. In greater detail, the peptides were synthesized by coupling each amino acid starting from a C-terminus by Fmoc solid phase peptide synthesis (SPPS) using ASP48S (Peptron, Inc., Daejeon ROK). Peptides with their first amino acid at the C-terminus attached to resin were used and were as follows:

NH2-Lys(Boc)-2-chloro-Trityl Resin
NH2-Ala-2-chloro-Trityl Resin
NH2-Arg(Pbf)-2-chloro-Trityl Resin All the amino acid materials used to synthesize the peptides were protected by Fmoc at the N-terminus, and the amino acid residues were protected by Trt, Boc, t-Bu (t-butylester), Pbf (2,2,4,6,7-pentamethyl dihydro-benzofuran-5-sulfonyl), or the like, which may be eliminated by an acid. Examples include:

Fmoc-Ala-OH, Fmoc-Arg(Pbf)-OH, Fmoc-Glu(OtBu)-OH, Fmoc-Pro-OH, Fmoc-Leu-OH, Fmoc-Ile-OH, Fmoc-Phe-OH, Fmoc-Ser(tBu)-OH, Fmoc-Thr(tBu)-OH, Fmoc- Lys(Boc)-OH, Fmoc-Gln(Trt)-OH, Fmoc-Trp(Boc)-OH, Fmoc-Met-OH, Fmoc-Asn(Trt)-OH, Fmoc-Tyr(tBu)-OH, Fmoc-Ahx-OH, and Trt-Mercaptoacetic acid.

HBTU[2-(1H-Benzotriazole-1-yl)-1,1,3,3-tetamethylaminium hexafluorophosphate]/HOBt [N-Hydroxybenzotriazole]/NMM [4-Methylmorpholine] were used as the coupling reagents. Piperidine in 20% DMF was used to remove Fmoc. In order to remove the protection from a residue or to separate the synthesized peptides from resin, a cleavage cocktail [trifluoroacetic acid (TFA)/triisopropylsilane (TIS)/ ethanedithiol (EDT)/$H_2O$=92.5/2.5/2.5/2.5] was used.

The peptide was synthesized by using the solid phase scaffold combined to the starting amino acid with the amino acid protection, reacting the corresponding amino acids separately, washing with solvent and deprotecting, and repeating the process. After cutting off the synthesized peptide from the resin, it was purified by HPLC and verified for synthesis by MS, and then freeze-dried.

Detailed processes are described below with reference to an example of Pep 1 (EARPALLTSRLRFIPK) consisting of SEQ ID NO: 1.

1) Coupling

Protected amino acids (8 equivalent) and the coupling agent HBTU (8 equiv.)/HOBt (8 equiv.)/NMM (16 equiv.) were melted in DMF and then added to $NH_2$-Lys(Boc)-2-chloro-trityl resin. A resultant obtained therefrom was allowed to react at room temperature for 2 hours, and then a reacted product obtained therefrom was washed with DMF, MeOH, and DMF, in the stated order.

2) Fmoc Deprotection

20% piperidine in DMF was added to the resultant mixture obtained from 1) and reacted twice at room temperature for 5 minutes each. Then, a resultant obtained therefrom was washed with DMF, MeOH, and DMF, in the stated order.

3) Processes in 1) and 2) were repeated to make a basic framework of peptide ($NH_2$-E(OtBu)-A-R(Pbf)-P-A-L-L-T(tBu)-S(tBu)-R(Pbf)L-R(Pbf)-F-I-P-K(Boc)-2-chloro-trityl resin) (SEQ ID NO: 2).

4) Cleavage: a cleavage cocktail was added to the resin coupled to the completely synthesized peptides and the peptides were separated from the resin.

5) Cooling diethyl ether was added to a mixture obtained from 4), and then the peptides were precipitated by using centrifugation.

6) After purification by Prep-HPLC, molecular weights of the peptides were checked by using LC/MS and the peptides were freeze-dried to produce powder.

Example 2: Methods of Preparation and Analysis of Materials (1) Preparation of Test Agent, PEP-1

PEP-1 (peptide of SEQ ID NO: 1), lyophilized white powder, obtained according to the method mentioned in example 1 was dissolved in 0.9% of saline, considering the correction factor of PEP-1 (purity: 94.13%, content: 92.36%, correction factor: 1.15). 50 mg/mL stock solution was further diluted into 20 mg/mL, 2 mg/mL, and 1 mg/mL with 0.9% saline, and stored at 4° C. for a week until the use.

(2) Preparation of Materials

The purpose of this example is to confirm the change of sexual hormones in blood from SD rats with 7 days repeated daily administration of SEQ ID NO: 1 peptide, PEP-1. This experiment followed the Ethics Regulation of Animal Test by KAMSI Inc. (Korea Animal Medical Science Institute). In addition, this experiment, Non-GLP experiment, referred to the MFDS (Ministry of Food and Drug Safety) notification; Agent 2013-40 ($5^{th}$ April 2013), Principles of Good Laboratory Practice (1997).

SPF Rats (Crlj:CD(SD)) were purchased from ORIENT-Bio Inc. (Mokdong-ri, Buk-myeon, Gapyeong-gun, Gyeonggi-do, Republic of Korea). 75 male (6.5 weeks old and 190~210 g) and 75 female (6.5 weeks old and 160~180 g) rats were monitored for 4 days, and 64 of male and female rats (each) were selected for the experiment. Raising condition is as follows; 23±3° C. of temperature, 5±15% of relative humidity, 10~20 times/hr of number of air changes, 12 hours (8 a.m.~8 p.m.) of lighting with 150~300 Lux of intensity.

Conditions in animal facility such as temperature-humidity, number of air changes, and intensity of lighting were regularly measured. Animal feed (manufactured from Cargill Agri Purina. Inc.) was purchased from DreamBios Co., Ltd (507, Gwangnaru-ro, Gwangjin-gu, Seoul, Republic of Korea), and given using the feeding system, allowed rats to eat freely. Purified water was given using polycarbonate water bottles, and bedding for rat cages was purchased from SaeronBio Inc. (800-17, Cheonggye-dong, Uiwang, Gyeonggi-do, Republic of Korea). A maximum of 5 rats were raised in each polycarbonate cage (W 170×L 235×H 125 mm) during acclimation, inspection, and administration procedures. Water, bedding and cages were replaced more than once a week.

(3) Animal Groups and Administration Routes 64 male and female mice (mentioned above) were divided into 8 groups. Administration regimen, for example, drugs, routes, dosages, and volumes were as follows:

TABLE 3

| Groups | Drugs (agent) | Dosage (mg/kg) | Volume (mL/kg) | Administration gap | Number of administrations | Sex | Number of mice | No. |
|---|---|---|---|---|---|---|---|---|
| G1 | Vehicle | — | 5 | 1/day | 7 | M | 8 | M01-08 |
| G2 | | — | | 1/day | 7 | F | 8 | F01-08 |
| G3 | PEP-1 | 5 | | 1/day | 7 | M | 8 | M09-16 |
| G4 | | 5 | | 1/day | 7 | F | 8 | F09-16 |
| G5 | | 10 | | 1/day | 7 | M | 8 | M17-24 |
| G6 | | 10 | | 1/day | 7 | F | 8 | F17-24 |
| G7 | | 10 | | 2/day | 4 | M | 8 | M25-32 |
| G8 | | 10 | | 2/day | 4 | F | 8 | F25-32 |
| G9 | | 10 | | *2/week | 2 | M | 8 | M33-40 |
| G10 | | 10 | | *2/week | 2 | F | 8 | F33-40 |
| G11 | | 100 | | 1/day | 7 | M | 8 | M41-48 |
| G12 | | 100 | | 1/day | 7 | F | 8 | F41-48 |
| G13 | | 100 | | *2/week | 2 | M | 8 | M49-56 |
| G14 | | 100 | | *2/week | 2 | F | 8 | F49-56 |
| G15 | | 250 | | 1/day | 7 | M | 8 | M57-64 |
| G16 | | 250 | | 1/day | 7 | F | 8 | F57-64 |

*Days of administration: first and seventh days

The detailed administration regimen is as follows; once a day, twice a day and twice a week in each experimental group. Injection initiated at 10 a.m. every day, and each rat was injected at one minute intervals. Rats in Group 9, 10, 13 and 14 were injected twice a week. Administration of high dose test agent preceded that of low dose. The volume of injection was calculated using recently measured weight of rats, and it was 5 mL/kg. Subcutaneous injection was performed as follows; assistant tilted the back of rat upward, and experimenter sterilized the back of rat with 70% alcohol, followed by subcutaneous injection of test agent with 26 G syringe.

(4) Blood Extraction 1.4 mL of blood sample (0.7 mL of serum) was collected after measurement of weight (Day 0). Next day (1 Day), 1.4 mL of blood sample (0.7 mL of serum) was collected twice after injection of test agent (4 hrs and 8 hrs after administration of test agent). For next 6 days (Day 2~Day 7), 1.4 mL of blood was extracted once everyday (4 hours after injection of test agent). Dose and volume of test agent of each group followed the Table 3, and injection time zone was same every day. Blood was extracted from the jugular vein, and left at room temperature for 30 minutes. Serum was separated using centrifugation (10,000 rpm for 5 minutes), and stored at −70±5° C. in Deep freezer until the use. Blood extraction from each subject was done in the same time zone every day.

(5) Hormonal Analysis Method

A CLIA (Chemi-Luminescence Immune Assay) Kit was used to analyze Testosterone, Estradiol E2, FSH (Follicle stimulating hormone), and LH (Luteinizing hormone). Analysis was completed within 48 hrs after blood extraction (Laboratory Medicine Department, Chung-Ang University Hospital), and detailed method is as follows; One-way ANOVA was used to verify the comparison between the vehicle and PEP-1, and between different doses of PEP-1. For further analysis, Duncan test was used as parametric test and Dunnett's test as non-parametric test. $p<0.05$ represents the statistical significance, and all statistical analysis was carried out with SPSS 10.1.

I. Analysis of Hormones

Example 3: Analysis of Testosterone

Figure 2:
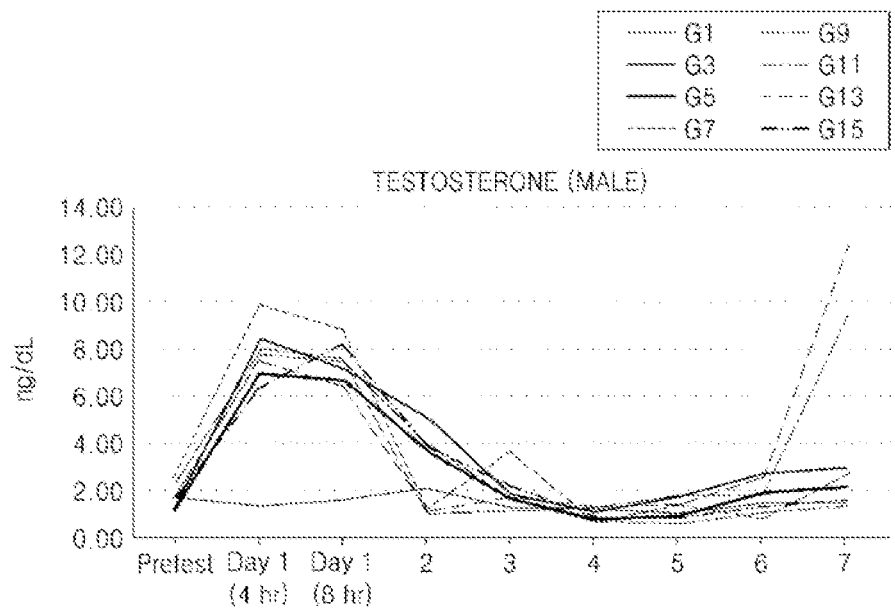
FIG. 2 is a graph showing changes in concentrations of testosterone in blood of male mice in which PEP-1 was repetitively administered, according to time.
Figure 3:
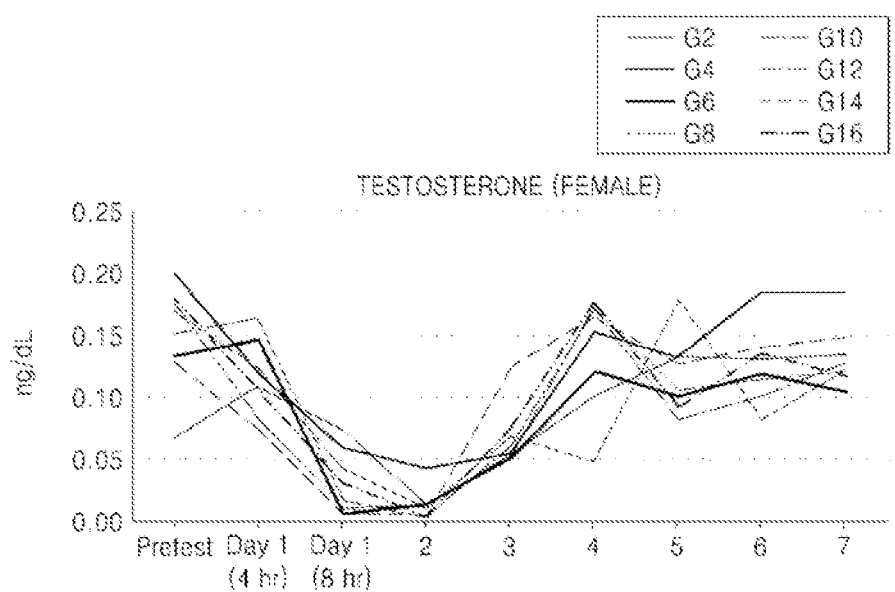
FIG. 3 is a graph showing changes in concentrations of testosterone in blood of female mice in which PEP-1 was repetitively administered, according to time.

Testosterone was analyzed using the samples prepared from example 2. 15 μL of serum was used for analysis. Fundamentals of analysis is competitive immunoassay based on direct chemi-luminescent. As mentioned in example 2, CLIA (Chemi-luminescence immune assay) Kit was used for Testosterone analysis, following the manufacture's protocol. Result is as follows; Testosterone level in all groups before injection of PEP-1 and/or vehicle was 1-3 ng/dL. At Day 1, Testosterone level increased up to 6-10 ng/dL in all groups injected with PEP-1 but vehicle group. At 2 Day, the Testosterone level was at the highest in G3, G5, G11 and G15 which received a once a day injection regimen. After Day 3, the Testosterone level decreased, and there was no significant difference between PEP-1 and vehicle, implicating that Testosterone level increased along the level of LH in the beginning, followed by going back to the normal level. In female groups, the baseline of Testosterone was too low to make significant findings. In addition, unlike the male group, Testosterone level before injection of PEP1 and/or vehicle was below 0.2 ng/dL in the female group and it further went down to 0.05 ng/dL after injection of PEP-1 followed by going back to normal level at Day 3. According to this, it could be concluded that PEP-1 does not have significant effect on the Testosterone level in female rat (Table 4 and, FIGS. 2 and 3).

TABLE 4

Testosterone level change in blood from rat after administration of PEP-1 (ng/dL, n = 8)

| Groups | Sex | Time | | | | | | | | |
|---|---|---|---|---|---|---|---|---|---|---|
| | | pre | 4 hr | 8 hr | 2 days | 3 days | 4 days | 5 days | 6 days | 7 days |
| G1 | Female | 1.57 | 1.28 | 1.54 | 2.05 | 1.23 | 1.21 | 0.99 | 1.41 | 1.45 |
| G3 | | 1.22 | 8.38 | 7.08 | 4.95 | 1.8 | 1.01 | 1.7 | 2.68 | 2.91 |
| G5 | | 1.15 | 6.87 | 6.59 | 3.56 | 1.57 | 0.67 | 0.81 | 1.8 | 2.1 |
| G7 | | 2.6 | 9.85 | 8.78 | 1.14 | 3.63 | 0.58 | 1.31 | 0.72 | 2.68 |
| G9 | | 2.3 | 7.92 | 7.57 | 0.9 | 1.05 | 1.21 | 1.73 | 1.67 | 9.43 |
| G11 | | 1.79 | 7.73 | 7.41 | 3.92 | 1.55 | 0.63 | 0.55 | 1.01 | 1.25 |
| G13 | | 1.71 | 7.48 | 6.34 | 0.97 | 1.65 | 1.25 | 1.3 | 2.54 | 12.35 |
| G15 | | 1.65 | 6.27 | 8.2 | 3.77 | 2.09 | 0.8 | 0.75 | 1.27 | 1.52 |
| G2 | Male | 0.07 | 0.11 | 0.07 | 0.01 | 0.05 | 0.1 | 0.13 | 0.13 | 0.14 |
| G4 | | 0.2 | 0.12 | 0.06 | 0.04 | 0.06 | 0.15 | 0.13 | 0.19 | 0.19 |
| G6 | | 0.13 | 0.15 | 0.01 | 0.01 | 0.05 | 0.12 | 0.1 | 0.12 | 0.11 |
| G8 | | 0.17 | 0.12 | 0.04 | 0.01 | 0.07 | 0.05 | 0.18 | 0.08 | 0.12 |
| G10 | | 0.15 | 0.16 | 0.02 | 0 | 0.06 | 0.17 | 0.08 | 0.1 | 0.13 |
| G12 | | 0.18 | 0.08 | 0.01 | 0.01 | 0.05 | 0.17 | 0.11 | 0.12 | 0.12 |
| G14 | | 0.13 | 0.07 | 0.01 | 0.01 | 0.13 | 0.17 | 0.13 | 0.14 | 0.15 |
| G16 | | 0.18 | 0.11 | 0.03 | 0 | 0.08 | 0.18 | 0.09 | 0.14 | 0.12 |

Example 4: Estradiol E2 Analysis

Figure 4:
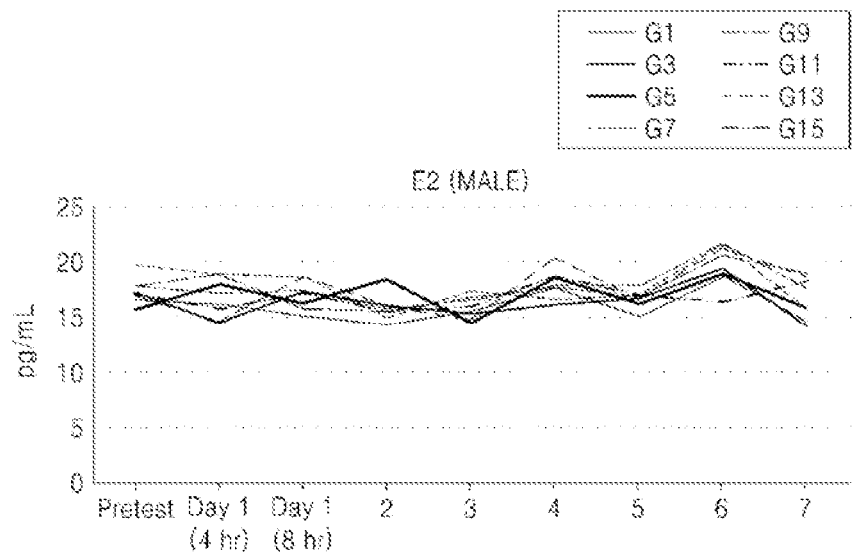
FIG. 4 is a graph showing changes in concentrations of estradiol (E2) in blood of male mice in which PEP-1 was repetitively administered, according to time.
Figure 5:
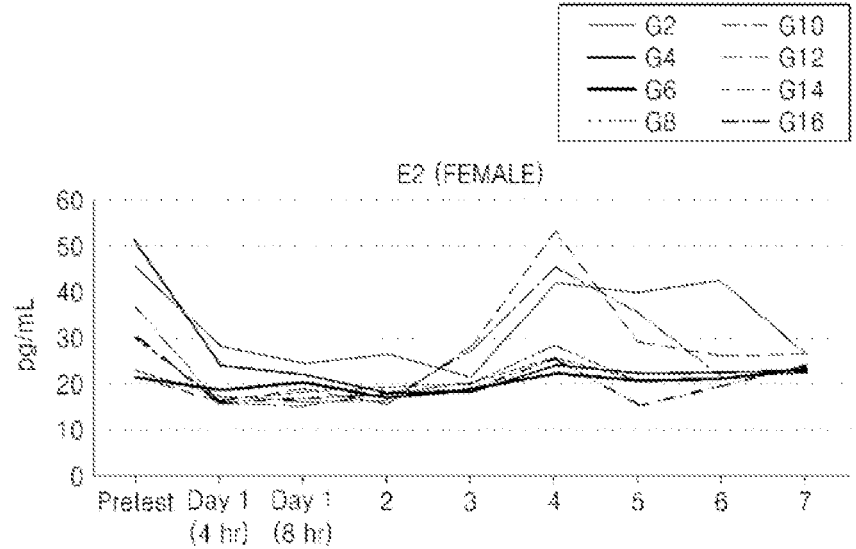
FIG. 5 is a graph showing changes in concentrations of estradiol (E2) in blood of female mice in which PEP-1 was repetitively administered, according to time.

Estradiol E2 was analyzed using the samples prepared from example 2. 75 μL of serum was used for analysis. Fundamentals of analysis is competitive immunoassay based on direct chemi-luminescent. As mentioned in example 2, CLIA (Chemi-luminescence immune assay) Kit was used, following the manufacture's protocol. The average level of Estradiol E2 in blood from male rat was lower than that of female, and initial level of Estradiol E2 (Before injection of PEP-1), 15-20 pg/mL, remained same until the Day 7, showing that PEP-1 does not have effect on Estradiol E2 level. However, in female group, the level of Estradiol E2 decreased from 20-50 pg/mL (baseline) to 16-30 pg/mL in all group injected with PEP-1 and/or vehicle at Day 1. This level remained the same until Day 3, and from Day 4 the Estradiol E2 level in G4, G10 and vehicle group increased up to 40-50 pg/mL followed by going back to normal level (Table 5, FIGS. 4, 5). To conclude, PEP-1 inhibited the Estradiol E2 level in the beginning in female group but the level recovered from Day 3-4, especially the number of injections and dose of test agent seem to correlate with inhibition of Estradiol E2 level.

TABLE 5

Estradiol E2 level change in blood from rat after administration of PEP-1 (pg/dL, n = 8)

| Group | Sex | Pre | 4 hr | 8 hr | 2 days | 3 days | 4 days | 5 days | 6 days | 7 days |
|---|---|---|---|---|---|---|---|---|---|---|
| G1 | Male | 16.49 | 16.25 | 15.13 | 14.34 | 15.57 | 17.78 | 15.06 | 18.76 | 14.59 |
| G3 | | 17.08 | 14.37 | 17.39 | 16.06 | 15.28 | 16.16 | 16.66 | 19.44 | 14.31 |
| G5 | | 15.64 | 17.97 | 16.26 | 18.52 | 14.46 | 18.61 | 16.24 | 18.96 | 15.85 |
| G7 | | 19.7 | 18.94 | 18.63 | 14.91 | 17.36 | 16.63 | 16.92 | 21.72 | 15.81 |
| G9 | | 17.9 | 18.9 | 15.62 | 15.6 | 16.83 | 17.69 | 16.85 | 20.63 | 19 |
| G11 | | 17.91 | 17.13 | 17.41 | 15.75 | 16.47 | 17.86 | 17.89 | 21.73 | 17.72 |
| G13 | | 16.84 | 14.6 | 18.64 | 15.94 | 14.67 | 20.51 | 16.58 | 21.31 | 18.68 |
| G15 | | 17.09 | 15.79 | 17.19 | 15.53 | 15.98 | 18.71 | 16.98 | 16.33 | 18.3 |
| G2 | Female | 45.5 | 28.16 | 24.52 | 26.55 | 21.29 | 41.61 | 39.84 | 42.39 | 25.99 |
| G4 | | 50.83 | 23.89 | 21.93 | 17.92 | 18.19 | 24.17 | 22.11 | 22.5 | 22.94 |
| G6 | | 21.41 | 18.79 | 20.11 | 16.84 | 18.59 | 22.32 | 20.87 | 21.27 | 23.14 |
| G8 | | 29.99 | 16.35 | 18.29 | 19.01 | 20.14 | 25.68 | 20.65 | 21.28 | 23.61 |
| G10 | | 22.91 | 17.27 | 16.1 | 16.39 | 27.35 | 45.55 | 35.5 | 21.45 | 22.39 |
| G12 | | 36.62 | 15.87 | 15.05 | 18.05 | 19.94 | 28.48 | 20.35 | 20.92 | 22.61 |
| G14 | | 21.46 | 16.4 | 18.96 | 15.46 | 28.33 | 53.29 | 29.31 | 25.87 | 26.45 |
| G16 | | 30.05 | 15.85 | 16.93 | 17.41 | 18.76 | 25.38 | 15.15 | 18.98 | 24.08 |

Example 5: FSH Analysis

FSH was analyzed using the samples prepared from example 2. 100 µL of serum was used for analysis. Fundamentals of analysis is Two-site sandwich immunoassay based on direct chemi-luminescent. As mentioned in example 2, CLIA (Chemi-luminescence immune assay) Kit was used, following the manufacture's protocol.

Figure 6:
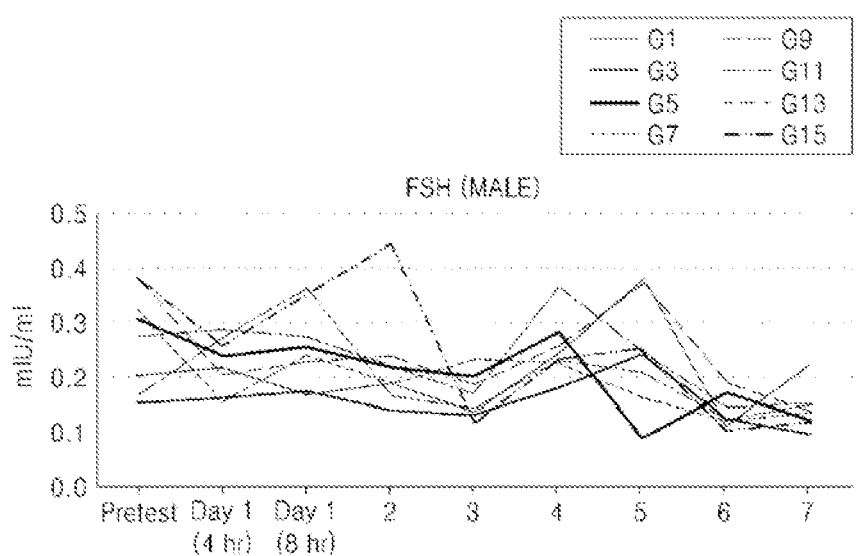
FIG. 6 is a graph showing changes in concentrations of FSH in blood of male mice in which PEP-1 was repetitively administered, according to time.
Figure 7:
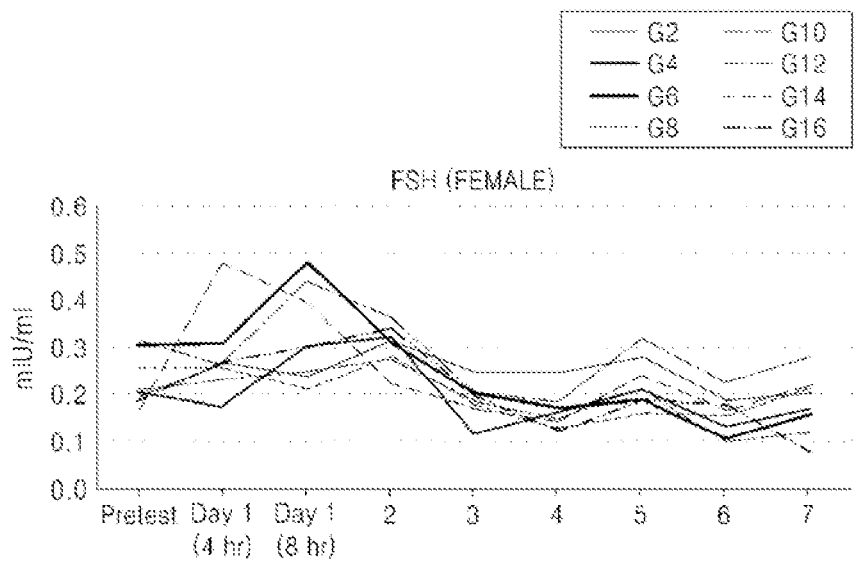
FIG. 7 is a graph showing changes in concentrations of FSH in blood of female mice in which PEP-1 was repetitively administered, according to time.

As the result of analysis, there was a slight increase, (at Day 1, 4 hr and 8 hr post injection) in particular with the administration of high doses (from G11 to G16 groups) in FSH level in both male and female with administration of PEP-1, compared to baseline (before injection) (Table 6, FIGS. 6, 7). On Day 1, the level of FSH from G6 and G14 increased compared to that of vehicle.

As the result of analysis, PEP-1 seems to stimulate the LH secretion from both male and female, and especially the level of LH increased by high dose and frequent injection of PEP-1. The LH level of male before administration of PEP-1 was 0.1 mIU/mL, and it increased up to 0.5-1.5 mIU/mL in all groups but vehicle at 4 hrs. The level of LH was the highest in G5, G11, and G15 which had every day administration regimen. After 8 hrs, the level of LH decreased

TABLE 6

FSH level change in blood from rat after administration of PEP-1 (mIU/mL, n = 8)

| Group | Sex | pre | 4 hr | 8 hr | 2 days | 3 days | 4 days | 5 days | 6 days | 7 days |
|---|---|---|---|---|---|---|---|---|---|---|
| G1 | Male | 0.20 | 0.22 | 0.17 | 0.19 | 0.14 | 0.24 | 0.38 | 0.11 | 0.22 |
| G3 | | 0.15 | 0.16 | 0.18 | 0.14 | 0.13 | 0.18 | 0.24 | 0.12 | 0.10 |
| G5 | | 0.31 | 0.24 | 0.25 | 0.22 | 0.20 | 0.28 | 0.09 | 0.17 | 0.12 |
| G7 | | 0.32 | 0.16 | 0.24 | 0.19 | 0.23 | 0.23 | 0.16 | 0.12 | 0.13 |
| G9 | | 0.28 | 0.29 | 0.28 | 0.22 | 0.17 | 0.37 | 0.25 | 0.14 | 0.15 |
| G11 | | 0.17 | 0.27 | 0.36 | 0.17 | 0.14 | 0.23 | 0.21 | 0.12 | 0.15 |
| G13 | | 0.38 | 0.21 | 0.23 | 0.24 | 0.19 | 0.26 | 0.37 | 0.19 | 0.14 |
| G15 | | 0.38 | 0.26 | 0.35 | 0.44 | 0.12 | 0.23 | 0.25 | 0.1 | 0.12 |
| G2 | Female | 0.20 | 0.27 | 0.24 | 0.32 | 0.25 | 0.25 | 0.28 | 0.19 | 0.2 |
| G4 | | 0.20 | 0.17 | 0.30 | 0.32 | 0.12 | 0.17 | 0.21 | 0.13 | 0.17 |
| G6 | | 0.31 | 0.31 | 0.48 | 0.31 | 0.20 | 0.17 | 0.19 | 0.1 | 0.16 |
| G8 | | 0.26 | 0.26 | 0.21 | 0.28 | 0.18 | 0.13 | 0.16 | 0.15 | 0.21 |
| G10 | | 0.31 | 0.26 | 0.44 | 0.37 | 0.21 | 0.18 | 0.32 | 0.23 | 0.28 |
| G12 | | 0.21 | 0.23 | 0.25 | 0.28 | 0.19 | 0.15 | 0.21 | 0.1 | 0.12 |
| G14 | | 0.17 | 0.48 | 0.4 | 0.23 | 0.17 | 0.14 | 0.24 | 0.17 | 0.22 |
| G16 | | 0.19 | 0.27 | 0.3 | 0.34 | 0.20 | 0.12 | 0.19 | 0.18 | 0.08 |

Example 6: LH Analysis

Figure 8:
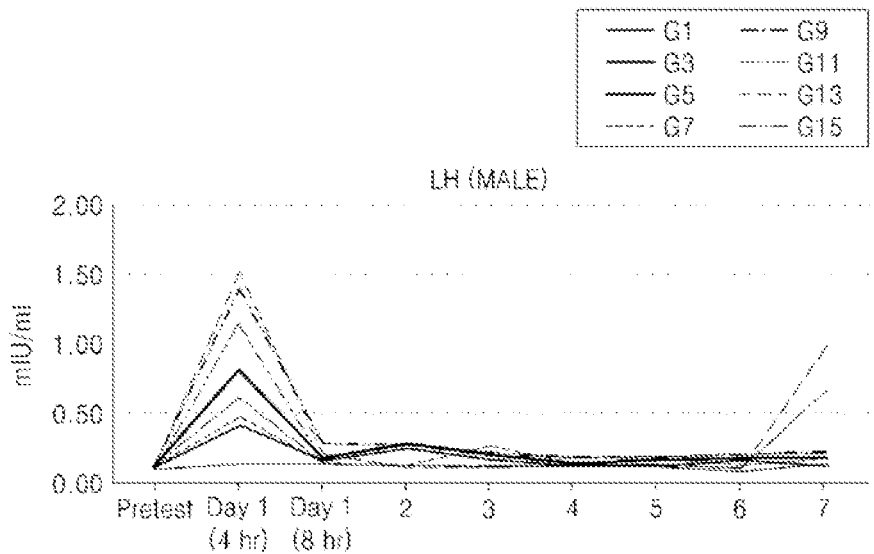
FIG. 8 is a graph showing changes in concentrations of LH in blood of male mice in which PEP-1 was repetitively administered, according to time.
Figure 9:
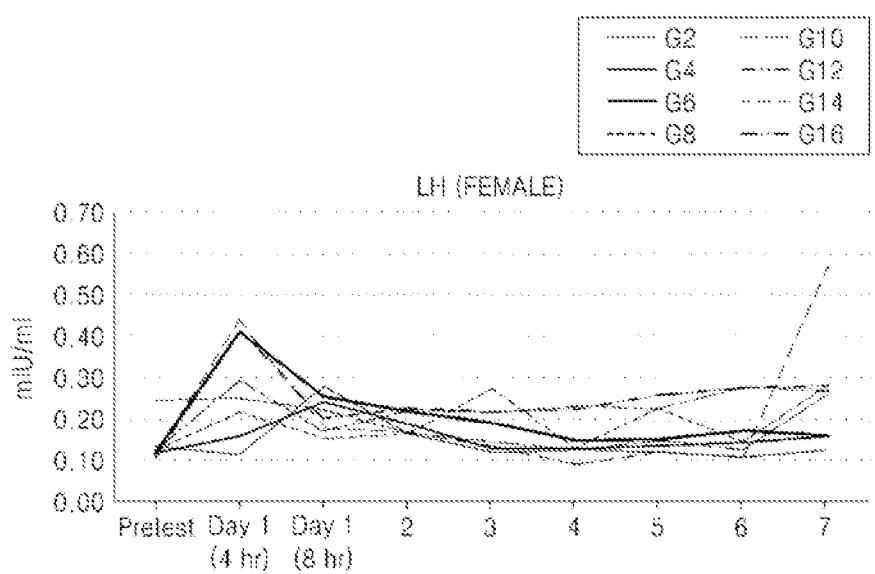
FIG. 9 is a graph showing changes in concentrations of LH in blood of female mice in which PEP-1 was repetitively administered, according to time.

LH was analyzed using the samples prepared from example 2. 50 µL of serum was used for analysis. Fundamentals of analysis is Two-site sandwich immunoassay based on direct chemi-luminescent. As mentioned in example 2, CLIA (Chemi-luminescence immune assay) Kit was used, following the manufacture's protocol.

rapidly, and remained the normal level until the end. In female rat, LH level also increased at 4 hr, but the extent of increase was not great apart from those in G12, G14, and G16 which had high dose regimen. Again, after 8 hrs the level of LH went back to normal level (Table 7, FIGS. 8, 9).

TABLE 7

LH level change in blood from rat after administration of PEP-1 (mIU/mL, n = 8)

| Group | Sex | pre | 4 hr | 8 hr | 2 days | 3 days | 4 days | 5 days | 6 days | 7 days |
|---|---|---|---|---|---|---|---|---|---|---|
| G1 | Male | 0.1 | 0.13 | 0.14 | 0.12 | 0.12 | 0.12 | 0.11 | 0.09 | 0.14 |
| G3 | | 0.12 | 0.42 | 0.16 | 0.24 | 0.17 | 0.12 | 0.13 | 0.16 | 0.13 |
| G5 | | 0.12 | 0.82 | 0.18 | 0.29 | 0.21 | 0.15 | 0.17 | 0.18 | 0.18 |
| G7 | | 0.12 | 0.48 | 0.14 | 0.12 | 0.27 | 0.14 | 0.18 | 0.13 | 0.17 |
| G9 | | 0.12 | 0.62 | 0.14 | 0.12 | 0.12 | 0.13 | 0.14 | 0.11 | 0.67 |
| G11 | | 0.1 | 1.16 | 0.18 | 0.28 | 0.23 | 0.18 | 0.19 | 0.21 | 0.21 |
| G13 | | 0.12 | 1.52 | 0.21 | 0.11 | 0.11 | 0.14 | 0.13 | 0.11 | 0.99 |
| G15 | | 0.12 | 1.4 | 0.29 | 0.28 | 0.2 | 0.19 | 0.2 | 0.21 | 0.23 |
| G2 | Female | 0.13 | 0.12 | 0.28 | 0.17 | 0.12 | 0.13 | 0.12 | 0.11 | 0.13 |
| G4 | | 0.12 | 0.16 | 0.24 | 0.19 | 0.13 | 0.13 | 0.14 | 0.14 | 0.16 |
| G6 | | 0.12 | 0.41 | 0.26 | 0.22 | 0.19 | 0.15 | 0.15 | 0.17 | 0.16 |
| G8 | | 0.13 | 0.22 | 0.15 | 0.17 | 0.28 | 0.13 | 0.23 | 0.15 | 0.28 |
| G10 | | 0.25 | 0.25 | 0.23 | 0.17 | 0.14 | 0.13 | 0.15 | 0.12 | 0.26 |
| G12 | | 0.13 | 0.3 | 0.17 | 0.22 | 0.22 | 0.23 | 0.23 | 0.28 | 0.27 |
| G14 | | 0.12 | 0.44 | 0.18 | 0.17 | 0.14 | 0.09 | 0.12 | 0.11 | 0.57 |
| G16 | | 0.11 | 0.42 | 0.2 | 0.23 | 0.22 | 0.23 | 0.26 | 0.28 | 0.28 |

Example 7: GnRH Analysis (1) Injection of PEP-1 into Mice

Sprague-Dawley (SD) rats were obtained from Orient Bio (Gyronggi-do, South Korea), and seven-week-old rats were used for the study. Rats were grouped into 4 (G1-G4) as shown in table 8, below. Rat were administered by subcutaneous (sc) injection of PEP-1 (100 mg/kg) twice (at Day 1 and at Day 7) during the seven day study period. Blood samples (1.4 mL) were collected at Day 0 (before the administration of PEP-1), at Day 1 (4 hr and 8 hr post injection), and at Day 7 (4 hr post injection). Serum samples obtained from the blood were used for the experiment. Serum samples prepared from the blood collected at Day 1 (4 hr post injection) were used for the experiment. The animal care and procedures were approved and in accordance with the Korea Animal Medical Science Institute (KAMSI) IACUC.

TABLE 8

Animal groups

| Group | Dosage (mg/kg) | Sex | N |
|---|---|---|---|
| 1 | (—) | Male | 8 |
| 2 | (—) | Female | 8 |
| 3 | 100 | Male | 8 |
| 4 | 100 | Female | 8 |

(2) Real-Time qPCR

RNA isolation and cDNA synthesis from the serum samples. The external control, miRNeasy Serum/Plasma Spike-In Control was added in each serum sample prior to the RNA extraction. Total RNA was extracted and purified from serum samples using miRNeasy Serum/Plasma Kit (Qiagen, Valencia, Calif., USA) following manufacturer's instructions. First-strand cDNA samples were synthesized from total RNAs using the Reverse Transcription System (Promega, Madison, Wis., USA).

(3) Real-Time qPCR Experiment

Real-time qPCR was performed using the RT2 SYBR Green qPCR Mastermix kit (Qiagen) with a CFX96 Real-Time System (Bio-Rad, Hercules, Calif., USA). Data was analyzed by CFX Manager™ Software V3.0 using the ΔΔCt method.

TABLE 9

Primers used for qRT-PCR anaysis

| Gene Name | | Sequence |
|---|---|---|
| GnRHR | S | 5'-CCCTCTTCTCATCATGCTAATCT-3' (SEQ ID NO: 3) |
| | AS | 5'-TGATTGACTGGCTCTGACAC-3' (SEQ ID NO: 4) |
| GNRH | S | 5' GTTCTGTTGACTGTGTGTTTGG-3' (SEQ ID NO: 5) |
| | AS | 5'-ATCTTCTTCTGCCCAGCTTC-3' (SEQ ID NO: 6) |
| LH | S | 5'-GGTCAGGGATAGAATGAGACAC-3' (SEQ ID NO: 7) |
| | AS | 5'-CGAACCATGCTAGGACAGTAG-3' (SEQ ID NO: 8) |
| FSH | S | 5'-CACCAGGGATCTGGTGTATAAG-3' (SEQ ID NO: 9) |
| | AS | 5'-ATTTCACCGAAGGAGCAGTAG-3' (SEQ ID NO: 10) |

(4) Serum Level of GnRH

Figure 10:
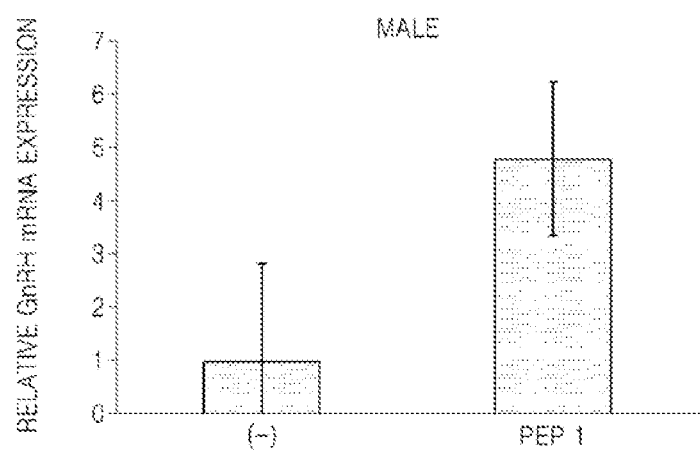
FIGS. 10 and 11 are graphs showing relative levels of GnRH mRNA expressions in male and female mice after administration of PEP-1.
Figure 11:
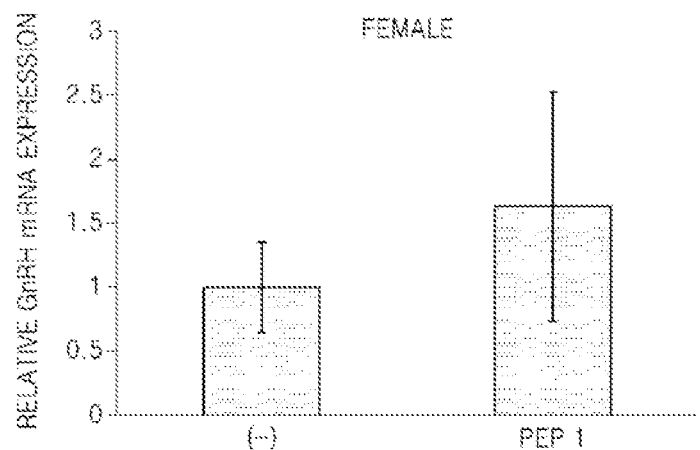

Rat serum samples obtained from the blood collected at 4 hr post-administration of PEP-1 (100 mg/kg) on the 1st day of the experiment were analyzed for the mRNA expression of gonadotropin-releasing hormone (GnRH). As shown in FIGS. 10 and 11, PEP-1 administration increased the relative GnRH mRNA expression both in male and female rats. The increase in GnRH levels observed in the serum samples was in accordance with the initial early burst in LH and FSH levels at 4 hr post-injection, At Day 1, as shown in FIGS. 6 to 9. Results showing that PEP-1 up-regulates GnRH mRNA levels support the potential therapeutic applications of PEP-1 as a GnRH agonist and/or analogue.

Through the analyses of such hormones, the sex hormone modulator according to an embodiment of the present invention is shown to have modulation effects on sex hormones including testosterone, estrogen, FSH, LH, and GnRH.

III. Treatment Effects of Hormone Modulator

Example 8: Analysis of Testosterone in Prostate Cell Line

When testosterone is injected into the body, testosterone becomes dihydrotestosterone (DHT) due to 5α-reductase, which stimulates the proliferation of prostate cells and induces benign prostatatic hyperplasia (BPH). Based on these facts, a PEP-1 (GV1001) injection experiment was performed for the inhibition of proliferation of prostatic cells in the following manner: The cell lines were mesenchymal cell lines (WPMY-1) and epithelial cell lines (RWPE-1) of prostates obtained from BPH animal models. WPMY-1 ($2.5 \times 10^3$ cells) and RWPE-1 ($1 \times 10^4$ cells) were seeded in a 96 well plate and changes in proliferation were observed in experimental groups in Table 10 below. Observation of changes in the proliferation was performed by suctioning a culture medium, adding 10 μL of CCK-8 solution to each well, and measuring an optical density at 450 nm for 1 hour to about 4 hours.

Figure 12:
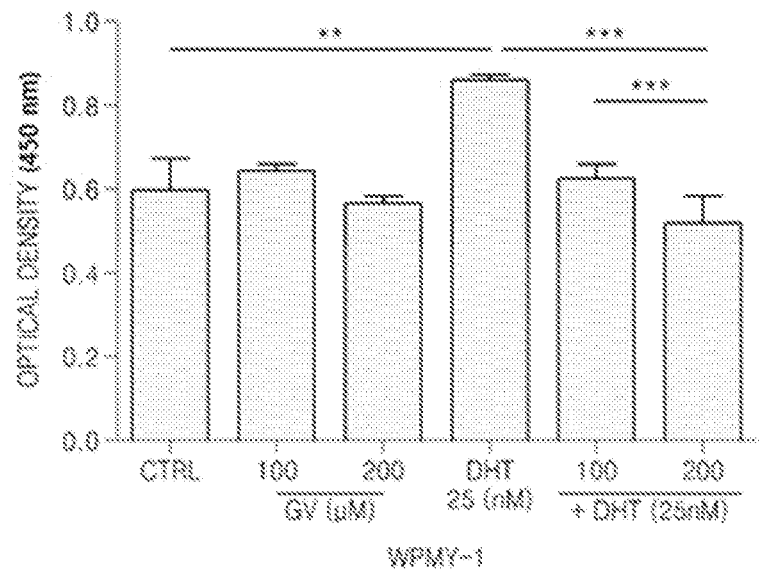
FIG. 12 is a graph showing levels of cell proliferation in mesenchymal cell lines (WPMY-1) of benign prostatic hyperplasia animal models treated with PEP-1 (GV1001)
Figure 13:
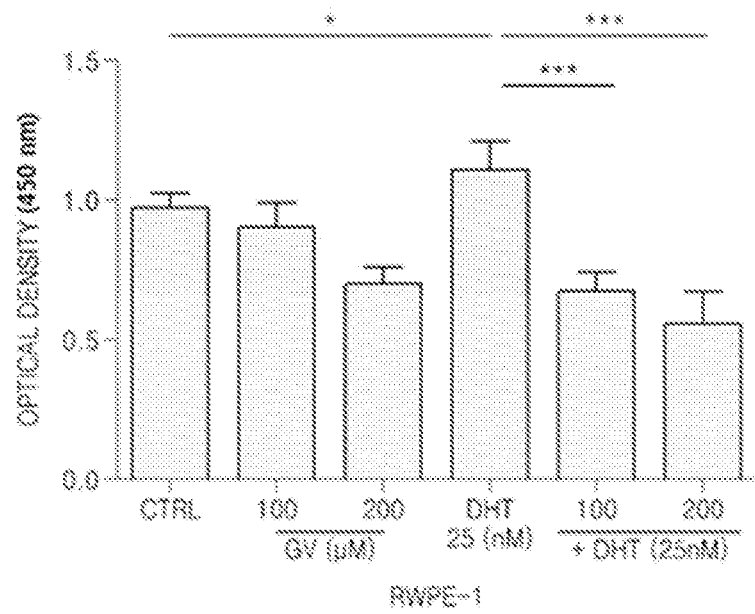
FIG. 13 is a graph showing levels of cell proliferation in epithelial cell lines (RWPE-1) of benign prostatic hyperplasia animal models treated with PEP-1 (GV1001).

Among the groups that were not treated with DHT (groups 1 to 3), a group that was not administered with PEP-1 (GV1001) (group 1) and groups administered with PEP-1 (GV1001) (groups 2 and 3) did not show a substantial difference in optical densities in both mesenchymal cell lines (WPMY-1) and epithelial cell lines (RWPE-1). Among the groups treated with DHT (groups 4 to 6), a group that was not administered with PEP-1 (GV1001) (group 4) and groups that were administered with PEP-1 (GV1001) (groups 5 and 6) showed a substantial difference in inhibition effects on proliferation, in which the groups treated with PEP-1 (GV1001) showed substantial inhibition effects on proliferation (see Table 10 and FIGS. 12 and 13). Accordingly, PEP-1 may have effects on the inhibition of prostate cell proliferation, which affects BPH caused by DHT.

TABLE 10

Treatment of cell lines according to groups

| Groups (common to WPMY-1 and RWPE-1) | Treatments |
| --- | --- |
| 1 (CTRL) | Cell line alone |
| 2 (100) | Treatment of the cell line with 100 μM of GV1001 |
| 3 (200) | Treatment of the cell line with 200 μM of GV1001 |
| 4 (DHT25) | Simultaneous treatment of the cell lines with 25 nM of DHT |
| 5 (100) | Simultaneous treatment of the cell lines with GV1001 (100 μM) and DHT (25 nM) |
| 6 (200) | Simultaneous treatment of the cell lines with GV1001 (200 μM) and DHT (25 nM) |

Through cell experiments of the hormone modulators, it may be concluded that the hormone modulator according to an embodiment of the present invention have effects on treatment, alleviation, or prevention of diseases caused by excessive or deficient levels of hormones, such as BPH.

What is claimed is:

1. A method of increasing testosterone level in a male subject, or increasing follicle stimulating hormone (FSH), luteinizing hormone (LH), or gonadotropin-releasing hormone (GnRH) levels in a male or a female subject comprising administering to the subject an effective amount of the peptide of SEQ ID NO: 1.

2. The method of claim 1, wherein the administration is once a day.

3. The method of claim 1, wherein the administration is one to three times a day.

4. The method of claim 1, further comprising administering to the subject an adjuvant.

5. The method of claim 4, wherein the adjuvant is a granulocyte-macrophage colony-stimulating factor (GM-CSF).

6. The method of claim 5, wherein GM-CSF is administered at a dosage of about 7 mg to about 700 mg.

7. The method of claim 5, wherein GM-CSF is subcutaneously administered at about 1 minute to about 150 minutes before the administration of the peptide.

8. The method of claim 5, wherein GM-CSF is subcutaneously administered at about 5 minutes to about 80 minutes before the administration of the peptide.

9. The method of claim 5, wherein GM-CSF is subcutaneously administered at about 10 minutes to about 15 minutes before the administration of the peptide.

10. The method of claim 1, wherein the subject is selected from a group consisting of humans, dogs, chickens, pigs, cows, sheep, guinea pigs, and monkeys.

11. The method of claim 1, wherein the peptide of SEQ ID NO: 1 is administered through oral, rectal, transdermal, intravenous, intramuscular, intraperitoneal, intramedullary, epidural, or subcutaneous means.

12. The method of claim 1, wherein the peptide of SEQ ID NO: 1 is administered through the oral means.

13. The method of claim 12, wherein the peptide of SEQ ID NO: 1 is administered as tablets, pills, soft or hard capsules, granules, powders, solutions, or emulsions.

14. The method of claim 1, wherein the peptide of SEQ ID NO: 1 is administered as injections, drips, lotions, ointments, gels, creams, suspensions, emulsions, suppositories, patches, or sprays.

15. The method of claim 1, wherein the peptide of SEQ ID NO: 1 is administered at a dosage of about 0.1 µg/kg/day to about 1 g/kg/day.

16. The method of claim 1, wherein the peptide of SEQ ID NO: 1 is administered at a dosage of about 1 µg/kg/day to about 10 mg/kg/day.

17. The method of claim 1, wherein the peptide of SEQ ID NO: 1 is administered at a dosage of about 10 µg/kg/day to about 1 mg/kg/day.

18. The method of claim 1, wherein the peptide of SEQ ID NO: 1 is administered at a dosage of about 50 µg/kg/day to about 100 µg/kg/day.

19. A method of increasing testosterone level in a male subject comprising administering to the subject an effective amount of the peptide of SEQ ID NO: 1.

20. A method of increasing follicle stimulating hormone (FSH), luteinizing hormone (LH), or gonadotropin-releasing hormone (GnRH) levels in a male or a female subject comprising administering to the subject an effective amount of the peptide of SEQ ID NO: 1.

* * * * *

SEQUENCE LISTING

```
<160> NUMBER OF SEQ ID NOS: 10

<210> SEQ ID NO 1
<211> LENGTH: 16
<212> TYPE: PRT
<213> ORGANISM: Homo sapiens

<400> SEQUENCE: 1

Glu Ala Arg Pro Ala Leu Leu Thr Ser Arg Leu Arg Phe Ile Pro Lys
1               5                   10                  15

<210> SEQ ID NO 2
<211> LENGTH: 16
<212> TYPE: PRT
<213> ORGANISM: Artificial Sequence
<220> FEATURE:
<223> OTHER INFORMATION: modified SEQ ID 1
<220> FEATURE:
<221> NAME/KEY: MISC_FEATURE
<222> LOCATION: (1)..(1)
<223> OTHER INFORMATION: NH2-Glu(OtBu)
<220> FEATURE:
<221> NAME/KEY: MISC_FEATURE
<222> LOCATION: (3)..(3)
<223> OTHER INFORMATION: Arg(Pbf)
<220> FEATURE:
<221> NAME/KEY: MISC_FEATURE
<222> LOCATION: (8)..(8)
<223> OTHER INFORMATION: Thr(tBu)
<220> FEATURE:
<221> NAME/KEY: MISC_FEATURE
<222> LOCATION: (9)..(9)
<223> OTHER INFORMATION: Ser(tBu)
<220> FEATURE:
<221> NAME/KEY: MISC_FEATURE
<222> LOCATION: (10)..(11)
<223> OTHER INFORMATION: Arg(Pbf)Leu
<220> FEATURE:
<221> NAME/KEY: MISC_FEATURE
<222> LOCATION: (12)..(12)
<223> OTHER INFORMATION: Arg(Pbf)
<220> FEATURE:
<221> NAME/KEY: MISC_FEATURE
```

```
<222> LOCATION: (16)..(16)
<223> OTHER INFORMATION: Lys(Boc)-2-chloro-trityl resin

<400> SEQUENCE: 2

Glu Ala Arg Pro Ala Leu Leu Thr Ser Arg Leu Arg Phe Ile Pro Lys
1               5                   10                  15

<210> SEQ ID NO 3
<211> LENGTH: 23
<212> TYPE: DNA
<213> ORGANISM: Artificial Sequence
<220> FEATURE:
<223> OTHER INFORMATION: GnRHR primer (S)

<400> SEQUENCE: 3
ccctcttctc atcatgctaa tct                                          23

<210> SEQ ID NO 4
<211> LENGTH: 20
<212> TYPE: DNA
<213> ORGANISM: Artificial Sequence
<220> FEATURE:
<223> OTHER INFORMATION: GnRHR primer (AS)

<400> SEQUENCE: 4
tgattgactg gctctgacac                                              20

<210> SEQ ID NO 5
<211> LENGTH: 22
<212> TYPE: DNA
<213> ORGANISM: Artificial Sequence
<220> FEATURE:
<223> OTHER INFORMATION: GNRH primer (S)

<400> SEQUENCE: 5
gttctgttga ctgtgtgttt gg                                           22

<210> SEQ ID NO 6
<211> LENGTH: 20
<212> TYPE: DNA
<213> ORGANISM: Artificial Sequence
<220> FEATURE:
<223> OTHER INFORMATION: GNRH primer (AS)

<400> SEQUENCE: 6
atcttcttct gcccagcttc                                              20

<210> SEQ ID NO 7
<211> LENGTH: 22
<212> TYPE: DNA
<213> ORGANISM: Artificial Sequence
<220> FEATURE:
<223> OTHER INFORMATION: LH primer (S)

<400> SEQUENCE: 7
ggtcagggat agaatgagac ac                                           22

<210> SEQ ID NO 8
<211> LENGTH: 21
<212> TYPE: DNA
<213> ORGANISM: Artificial Sequence
<220> FEATURE:
<223> OTHER INFORMATION: LH primer (AS)

<400> SEQUENCE: 8
cgaaccatgc taggacagta g                                            21
```

```
<210> SEQ ID NO 9
<211> LENGTH: 22
<212> TYPE: DNA
<213> ORGANISM: Artificial Sequence
<220> FEATURE:
<223> OTHER INFORMATION: FSH primer (S)

<400> SEQUENCE: 9
caccagggat ctggtgtata ag                                            22

<210> SEQ ID NO 10
<211> LENGTH: 21
<212> TYPE: DNA
<213> ORGANISM: Artificial Sequence
<220> FEATURE:
<223> OTHER INFORMATION: FSH primer (AS)

<400> SEQUENCE: 10
atttcaccga aggagcagta g                                             21
```